US011034724B2

(12) United States Patent
Duncan

(10) Patent No.: US 11,034,724 B2
(45) Date of Patent: Jun. 15, 2021

(54) CRYSTALLINE SALT FORMS OF BOC-D-ARG-DMT-LYS-(BOC)-PHE-NH$_2$

(71) Applicant: Stealth BioTherapeutics Corp., Grand Cayman (KY)

(72) Inventor: Scott M. Duncan, Bedford, MA (US)

(73) Assignee: Stealth BioTherapeutics Corp., Grand Cayman (KY)

( * ) Notice: Subject to any disclaimer, the term of this patent is extended or adjusted under 35 U.S.C. 154(b) by 0 days.

(21) Appl. No.: 16/603,117

(22) PCT Filed: Apr. 4, 2018

(86) PCT No.: PCT/US2018/025990
§ 371 (c)(1),
(2) Date: Oct. 4, 2019

(87) PCT Pub. No.: WO2018/187400
PCT Pub. Date: Oct. 11, 2018

(65) Prior Publication Data
US 2020/0369724 A1    Nov. 26, 2020

Related U.S. Application Data

(60) Provisional application No. 62/481,766, filed on Apr. 5, 2017.

(51) Int. Cl.
*C30B 29/58* (2006.01)
*C07K 5/11* (2006.01)

(52) U.S. Cl.
CPC ............ *C07K 5/1019* (2013.01); *C30B 29/58* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 5,312,899 | A | 5/1994 | Schiller |
| 6,703,483 | B1 | 3/2004 | Schiller |
| 7,498,297 | B2 | 3/2009 | Szeto et al. |
| 7,576,061 | B2 | 8/2009 | Szeto et al. |
| 7,718,620 | B2 | 5/2010 | Szeto et al. |
| 7,732,398 | B2 | 6/2010 | Szeto et al. |
| 8,404,646 | B2 | 3/2013 | Schiller et al. |
| 8,957,030 | B2 | 2/2015 | Szeto et al. |
| 9,345,738 | B2 | 5/2016 | Wilson et al. |
| 9,549,963 | B2 | 1/2017 | Liu et al. |
| 9,561,258 | B2 | 2/2017 | Wilson |
| 9,636,378 | B2 | 5/2017 | Wilson |
| 9,982,014 | B2 | 5/2018 | Hirai et al. |
| 9,988,422 | B2 | 6/2018 | Wilson et al. |
| 10,188,692 | B2 | 1/2019 | Liu et al. |
| 10,188,693 | B2 | 1/2019 | Wilson et al. |
| 10,221,213 | B2 | 3/2019 | Wilson |
| 10,676,506 | B2 | 6/2020 | Duncan |
| 10,683,326 | B2 | 6/2020 | Duncan et al. |
| 2011/0177047 | A1 | 7/2011 | Liu et al. |
| 2012/0329730 | A1 | 12/2012 | Szeto et al. |
| 2013/0059784 | A1 | 3/2013 | Wilson |
| 2013/0196921 | A1 | 8/2013 | Wilson et al. |
| 2014/0044689 | A1 | 2/2014 | Liu et al. |
| 2014/0093897 | A1 | 4/2014 | Szeto et al. |
| 2015/0118315 | A1 | 4/2015 | Wilson |
| 2015/0359838 | A1 | 12/2015 | Szeto et al. |
| 2016/0030501 | A1 | 2/2016 | Borow et al. |
| 2016/0151446 | A1 | 6/2016 | Wilson |
| 2016/0228491 | A1 | 8/2016 | Wilson |
| 2016/0264623 | A1 | 9/2016 | Hirai et al. |
| 2017/0028015 | A1 | 2/2017 | Borow et al. |
| 2017/0081363 | A1 | 3/2017 | Wilson |
| 2017/0087204 | A1 | 3/2017 | Wilson et al. |
| 2017/0240593 | A1 | 8/2017 | Szeto et al. |
| 2018/0044378 | A1 | 2/2018 | Duncan et al. |
| 2019/0022165 | A1 | 1/2019 | Wilson |
| 2019/0022167 | A1 | 1/2019 | Wilson |
| 2019/0202861 | A1 | 7/2019 | Duncan et al. |
| 2019/0233474 | A1 | 8/2019 | Duncan |
| 2019/0382442 | A1 | 12/2019 | Duncan et al. |
| 2020/0369724 | A1 | 11/2020 | Duncan |

FOREIGN PATENT DOCUMENTS

| | | |
|---|---|---|
| WO | WO-2014/134554 A1 | 9/2014 |
| WO | WO-2014/134562 A1 | 9/2014 |
| WO | WO-2014/185952 A1 | 11/2014 |
| WO | WO-2014/209905 A2 | 12/2014 |
| WO | WO-2014/210056 A1 | 12/2014 |
| WO | WO-2014/210062 A1 | 12/2014 |
| WO | WO-2015/009414 A1 | 1/2015 |
| WO | WO-2015/017781 A1 | 2/2015 |

(Continued)

OTHER PUBLICATIONS

Thomas, Dolca A. et al, "Mictochondrial targeting with antioxidant peptide ss-31 prevents mitochondrial depolarizatio, reduces islet cell apoptosis, increases islet cell yield, andimproves posttransplantation function." J. Am. Soc. Nephrol. (2007) 18 p. 213-222.*
Carpino, Louis A. et al, "Rapid, continuous solution phase synthesis: application to peptides of pharmaceutical interest." Org. Process. Res. Devel. (2003) 7 p. 28-37.*
Wu, Peng et al, "Site-specific chemical modifications of recombinant porteins produced in mammalian cells by using the genetically encoded aldehyde tag." PNAS (2009) 106(9) p. 3000-3005.*
Extended European Search Report for EP Application No. EP 17764188 dated Sep. 18, 2019.
International Search Report and Written Opinion for International Application No. PCT/US17/21790 dated Jun. 5, 2017.

(Continued)

*Primary Examiner* — Fred H Reynolds
(74) *Attorney, Agent, or Firm* — Dana M. Gordon; Foley Hoag LLP

(57) ABSTRACT

Disclosed are various crystalline salt forms of Boc-D-Arg-DMT-Lys(Boc)-Phe-NH$_2$.

14 Claims, 14 Drawing Sheets

(56) References Cited

FOREIGN PATENT DOCUMENTS

| WO | WO-2015/017861 A1 | 2/2015 |
| WO | WO-2015/023680 A1 | 2/2015 |
| WO | WO-2015/100376 A1 | 7/2015 |
| WO | WO-2015/103577 A1 | 7/2015 |
| WO | WO-2015/134096 A1 | 9/2015 |
| WO | WO-2015/183988 A1 | 12/2015 |
| WO | WO-2015/183995 A2 | 12/2015 |
| WO | WO-2015/195737 A1 | 12/2015 |
| WO | WO-2016/001042 A1 | 1/2016 |
| WO | WO-2016/004067 A1 | 1/2016 |
| WO | WO-2016/004093 A2 | 1/2016 |
| WO | WO-2016/029027 A2 | 2/2016 |
| WO | WO-2016/144905 A1 | 9/2016 |
| WO | WO-2016/209261 A1 | 12/2016 |
| WO | WO-2017/151886 A1 | 9/2017 |
| WO | WO-2017/156403 A1 | 9/2017 |
| WO | WO-2017/201433 A1 | 11/2017 |
| WO | WO-2018/034901 A1 | 2/2018 |
| WO | WO-2018/187400 A1 | 10/2018 |
| WO | WO-2018/223032 A1 | 12/2018 |

OTHER PUBLICATIONS

International Search Report and Written Opinion for International Application No. PCT/US2018/025990 dated Jun. 19, 2018.
McPherson et al., "Introduction to protein crystallization," Acta Cryst F70:2-20 (2014).

* cited by examiner

CRYSTALLINE SALT FORMS OF BOC-D-ARG-DMT-LYS-(BOC)-PHE-NH$_2$

RELATED APPLICATIONS

This application is the U.S. National Stage of International Patent Application No. PCT/US2018/025990, filed Apr. 4, 2018, which claims the benefit of priority to U.S. Provisional Patent Application Ser. No. 62/481,766, filed Apr. 5, 2017.

BACKGROUND

Through oxidative phosphorylation, mitochondria convert nutrients and oxygen into adenosine triphosphate (ATP), the chemical transporter of energy in most aerobic organisms. The electron transport chain (ETC) of the mitochondria represent the primary source of ATP, as well as a source of reactive oxygen species (ROS). Mitochondrial dysfunction in a cell results in less ATP production and, as a result, insufficient energy to maintain the cell. Such dysfunction also results in excessive ROS production, spiraling cellular injury, and ultimately apoptosis of the cell. Accordingly, mitochondrial dysfunction is a key element believed to be at the root of a variety of serious, debilitating diseases.

Natural antioxidants, such as coenzyme Q and vitamin E, have been shown to provide some protection of the cell from damage induced by the elevated ROS levels associated with mitochondrial dysfunction. However, antioxidants or oxygen scavengers have also been shown to reduce ROS to unhealthy levels and may not reach the ETC in sufficient concentrations to correct the mitochondrial imbalance. Therefore, there is a need for novel compounds that can selectively target the ETC, restore efficient oxidative phosphorylation, and thereby address mitochondrial disease and dysfunction.

SUMMARY

Disclosed are various crystalline salt forms of Boc-D-Arg-DMT-Lys(Boc)-Phe-NH$_2$.

DETAILED DESCRIPTION

The present invention features salts of Compound I:

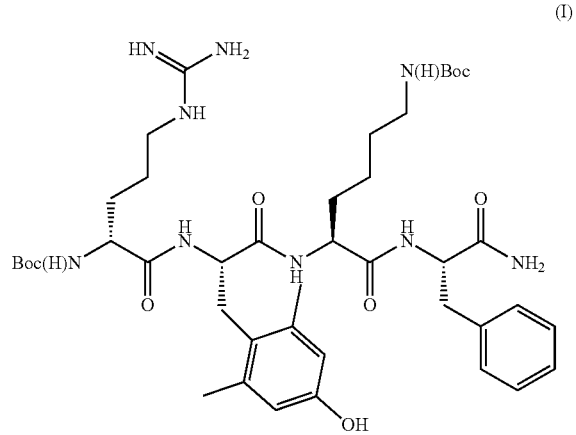

(I; Boc-D-Arg-DMT-Lys(Boc)-Phe-NH$_2$), wherein Boc-represents tert-butyl-O—C(O)—.

Compound I is a synthetic precursor of Compound II:

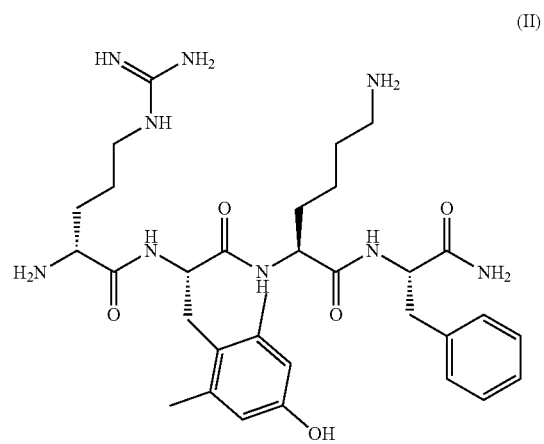 [SMILES: Cc1cc(O)cc(C)c1C[C@H](NC(=O)[C@H](N)CCCNC(=N)N)C(=O)N[C@@H](CCCCN)C(=O)N[C@@H](Cc1ccccc1)C(N)=O]

(II; MTP-131; D-Arg-DMT-Lys-Phe-NH$_2$) or a salt thereof. Compound II has been shown to affect the mitochondrial disease process by helping to protect organs from oxidative damage caused by excess ROS production, and to restore normal ATP production.

A crystalline form of a salt of Compound I can be used to modulate/improve the physicochemical properties of the compound, including but not limited to solid state properties (e.g., crystallinity, hygroscopicity, melting point, or hydration), pharmaceutical properties (e.g., solubility/dissolution rate, stability, or compatibility), as well as crystallization characteristics (e.g., purity, yield, or morphology).

In certain embodiments, the polymorph of the crystalline salt is characterized by X-ray powder diffraction (XRPD). θ represents the diffraction angle, measured in degrees. In certain embodiments, the diffractometer used in XRPD measures the diffraction angle as two times the diffraction angle θ. Thus, in certain embodiments, the diffraction patterns described herein refer to X-ray intensity measured against angle 2θ.

In certain embodiments, a crystalline salt of Compound (I) is not solvated (e.g., the crystal lattice does not comprise molecules of a solvent). In certain alternative embodiments, a crystalline salt of Compound (I) is solvated. In some cases, the solvent is water.

In one aspect, the invention features a crystalline form of Compound I which has characteristic peaks in the X-ray powder diffraction (XRPD) pattern as shown in any one of FIGS. 9-14.

In another aspect, the invention features a crystalline form of Compound I which has characteristic peaks in the X-ray powder diffraction (XRPD) pattern at values of two theta (° 2θ) as shown in any one of Tables A-F.

The relative intensity, as well as the two theta value, of each peak in Tables A-F, as well as FIGS. 9-14, may change or shift under certain conditions, although the crystalline form is the same. One of ordinary skill in the art should be able readily to determine whether a given crystalline form is the same crystalline form as described in one of Tables A-F as well as FIGS. 9-14 by comparing their XRPD data.

Figure 1:
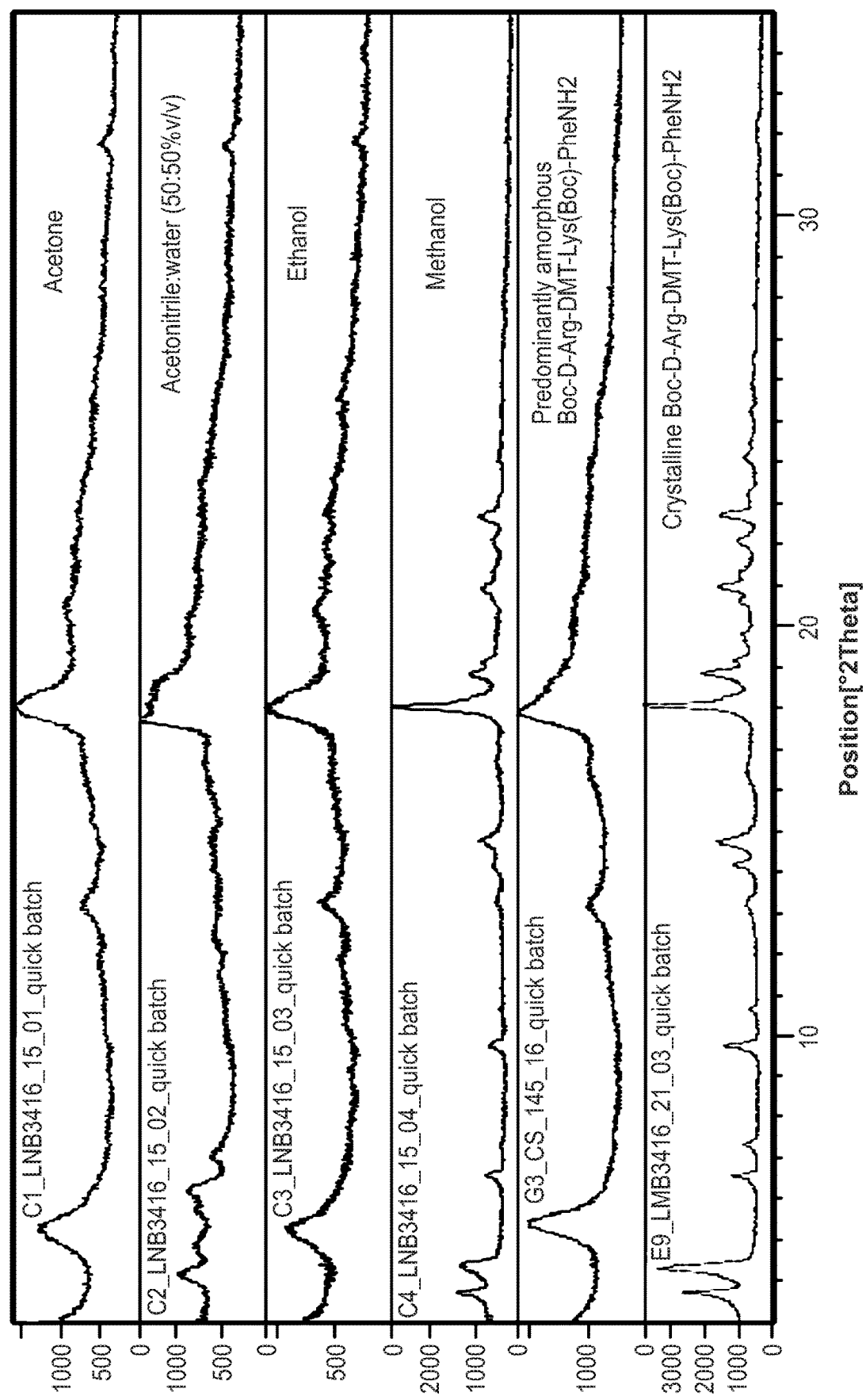
FIG. 1 depicts a XRPD pattern of a hydrochloride salt of Compound I.
Figure 2:
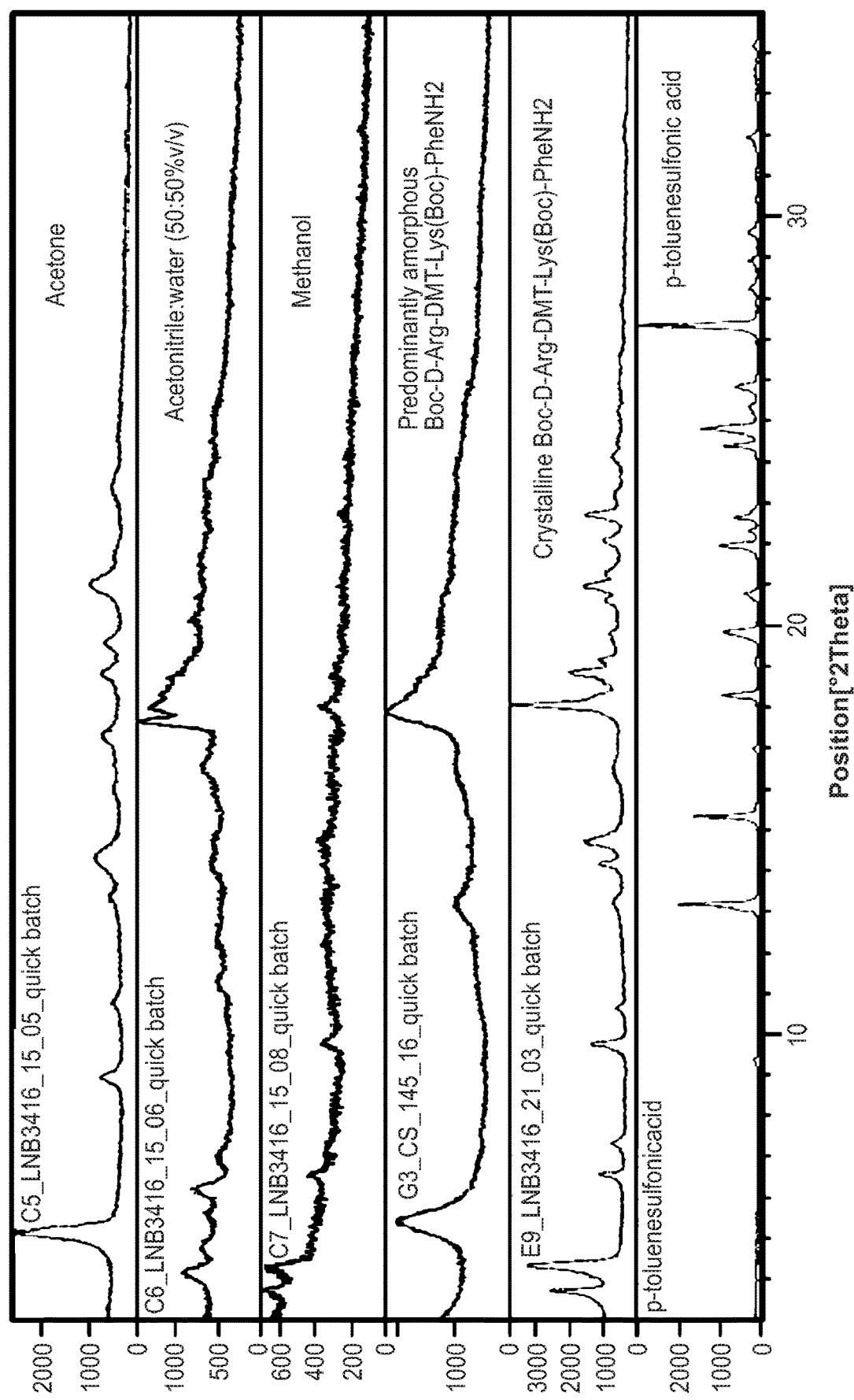
FIG. 2 depicts a XRPD pattern of a tosylate salt of Compound I.
Figure 3:
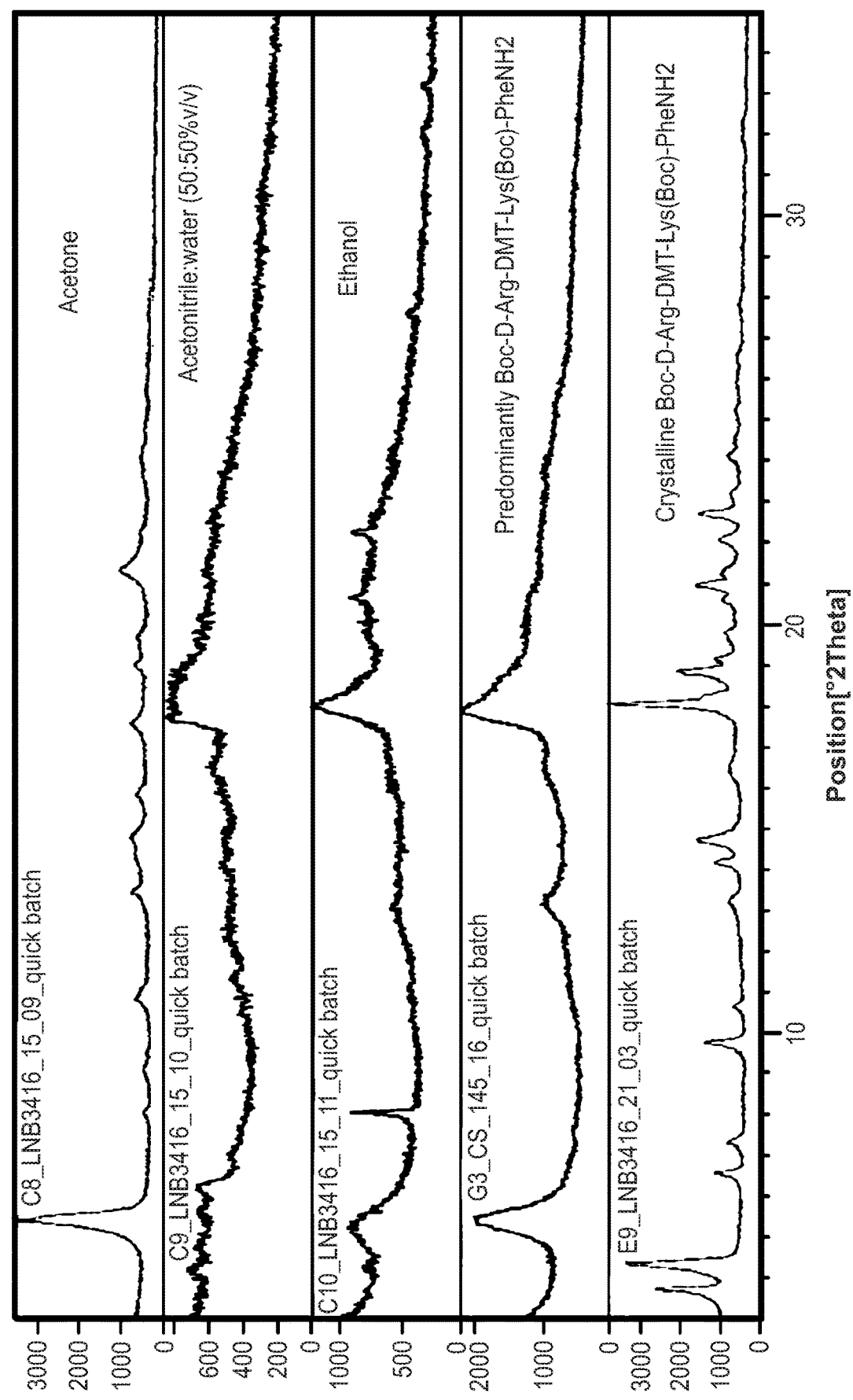
FIG. 3 depicts a XRPD pattern of a mesylate salt of Compound I.
Figure 4:
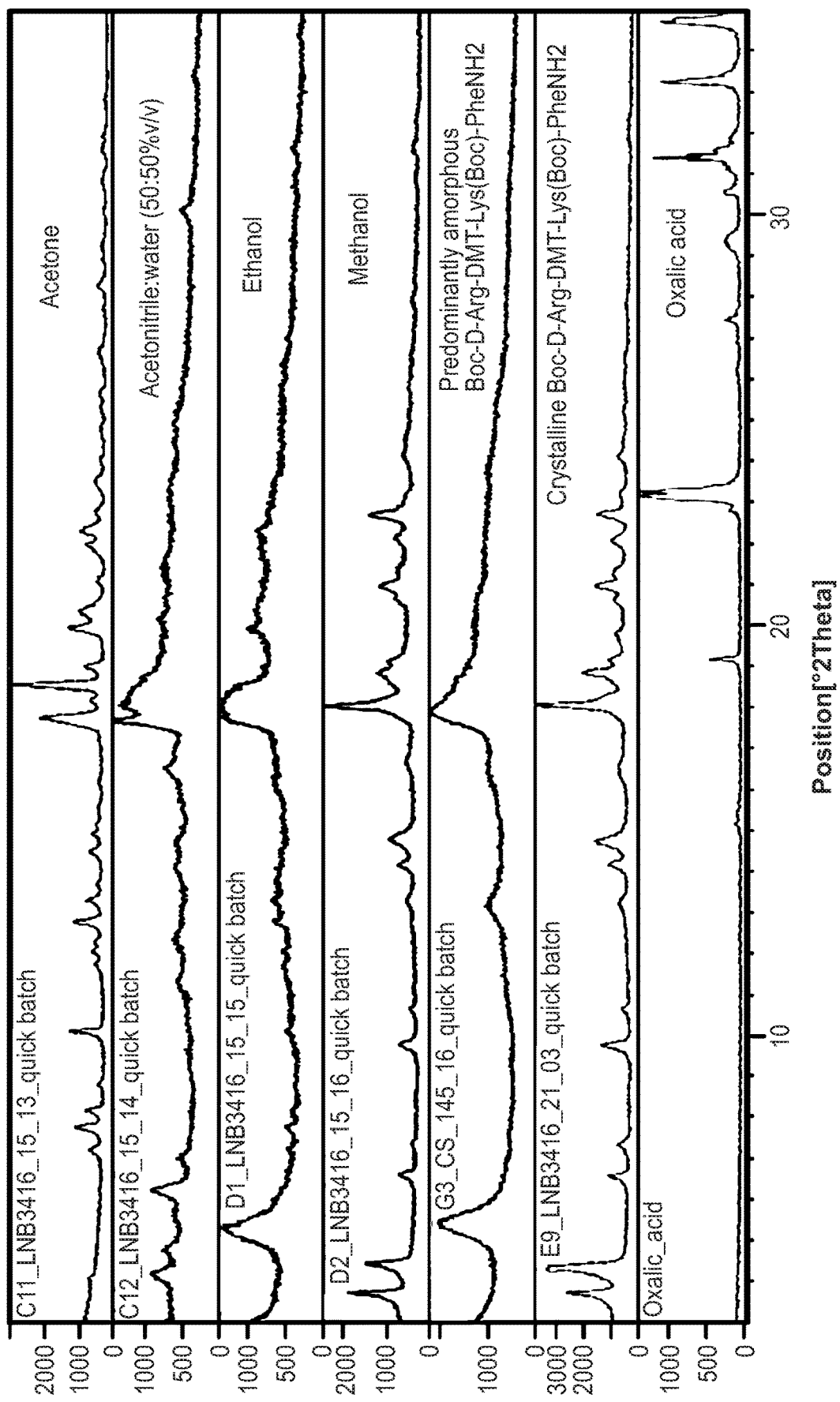
FIG. 4 depicts a XRPD pattern of an oxalate salt of Compound I.
Figure 5:
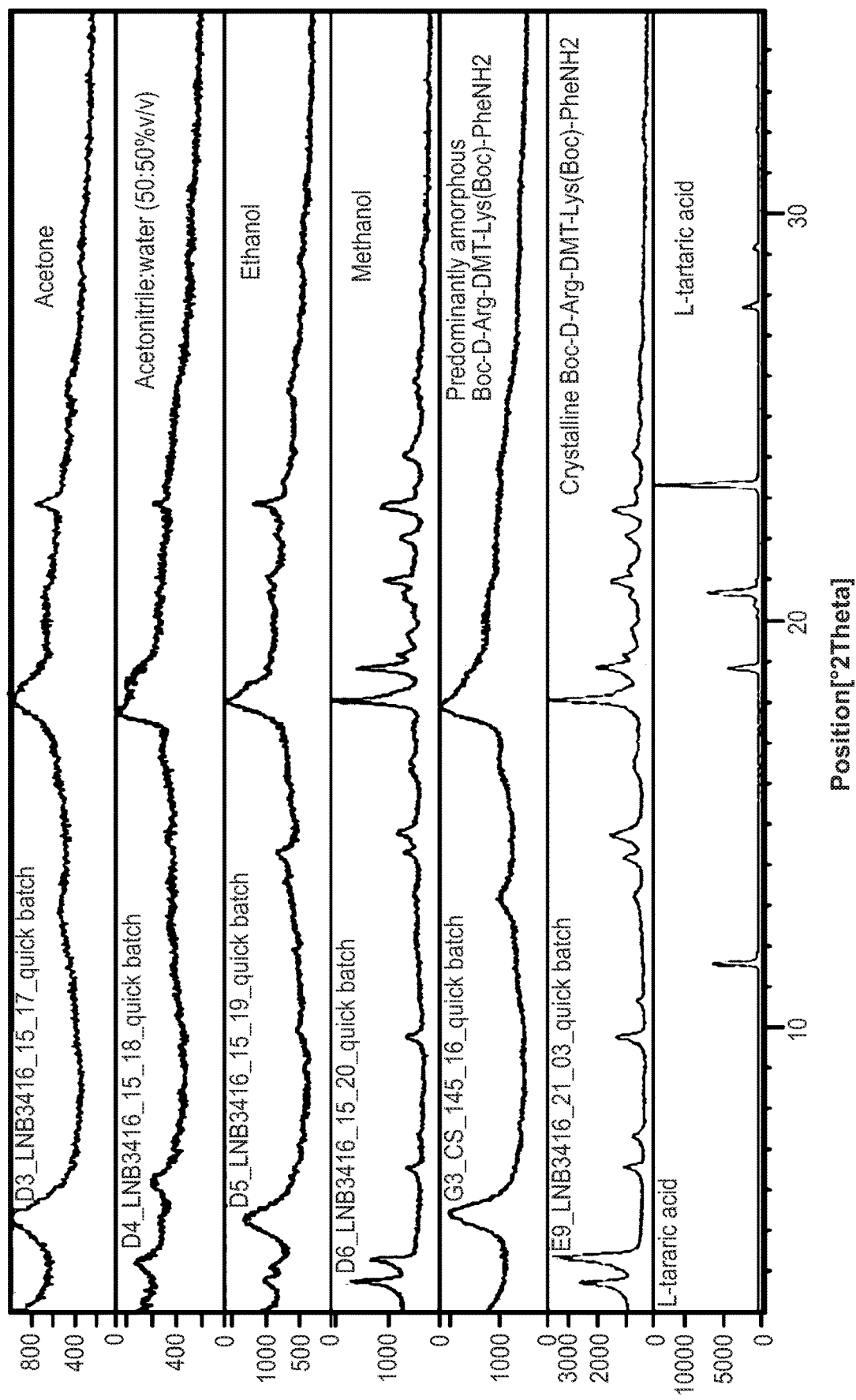
FIG. 5 depicts a XRPD pattern of a L-tartaric acid salt of Compound I.
Figure 6:
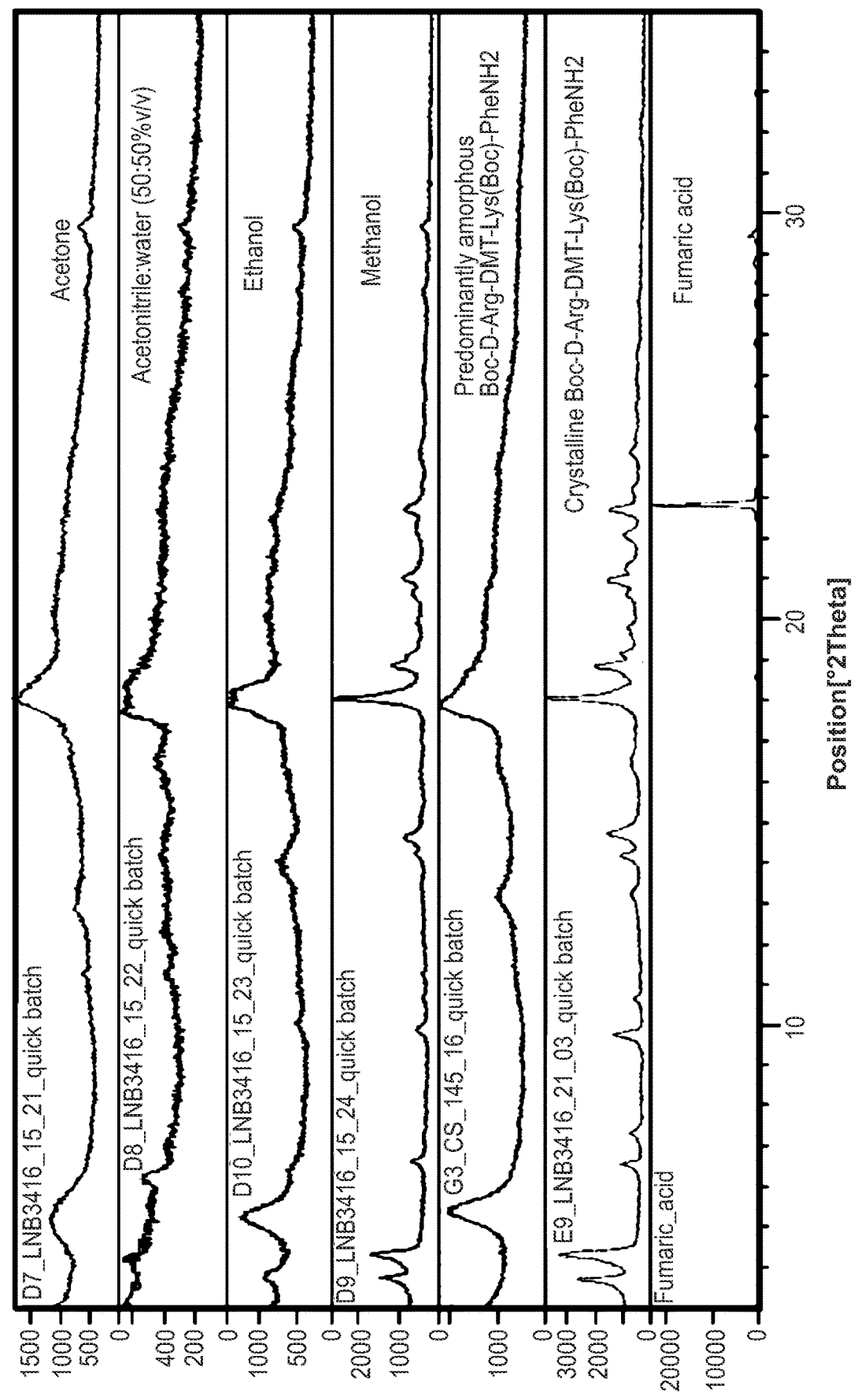
FIG. 6 depicts a XRPD pattern of a fumarate salt of Compound I.
Figure 7:
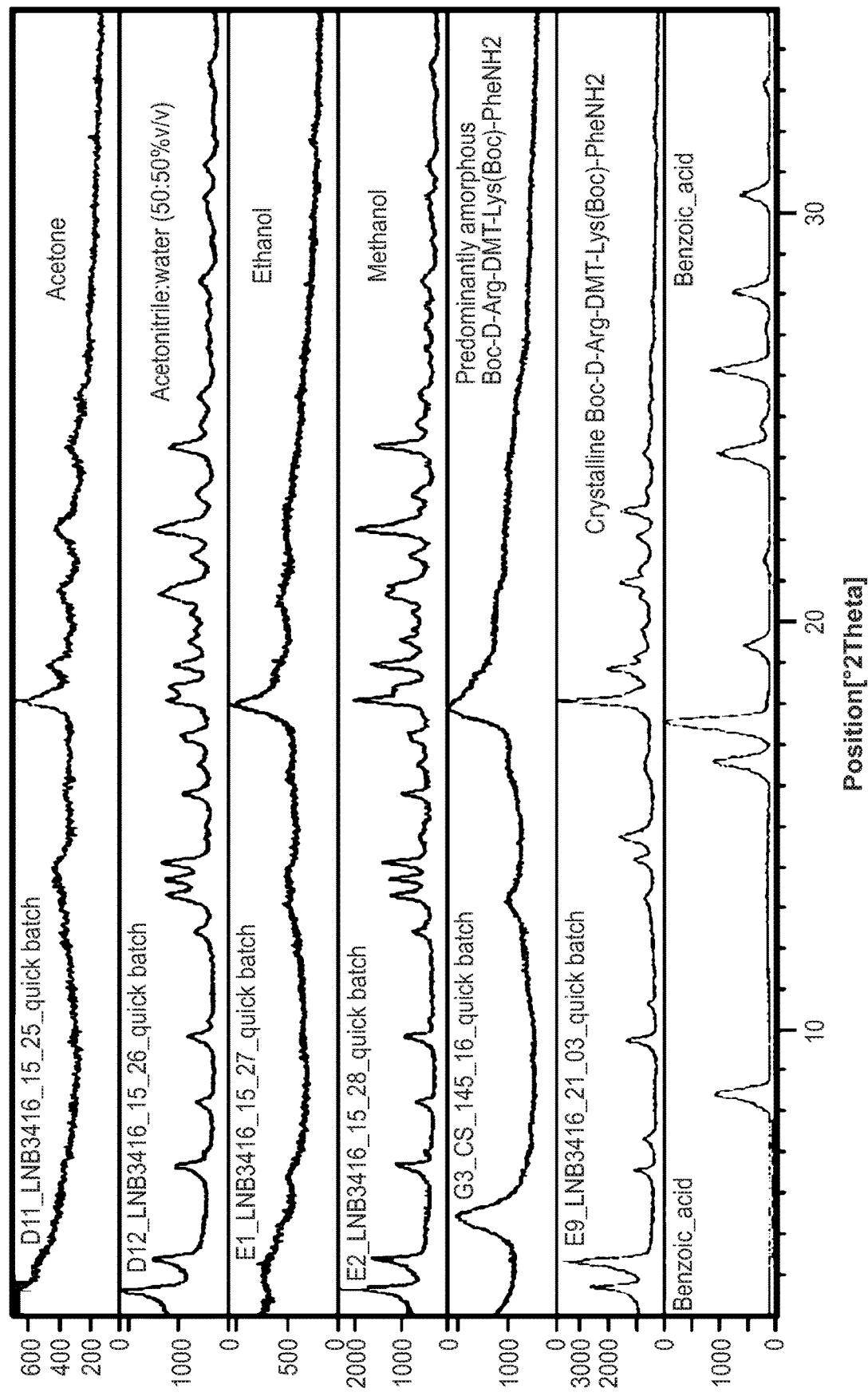
FIG. 7 depicts a XRPD pattern of a benzoic acid salt of Compound I.
Figure 8:
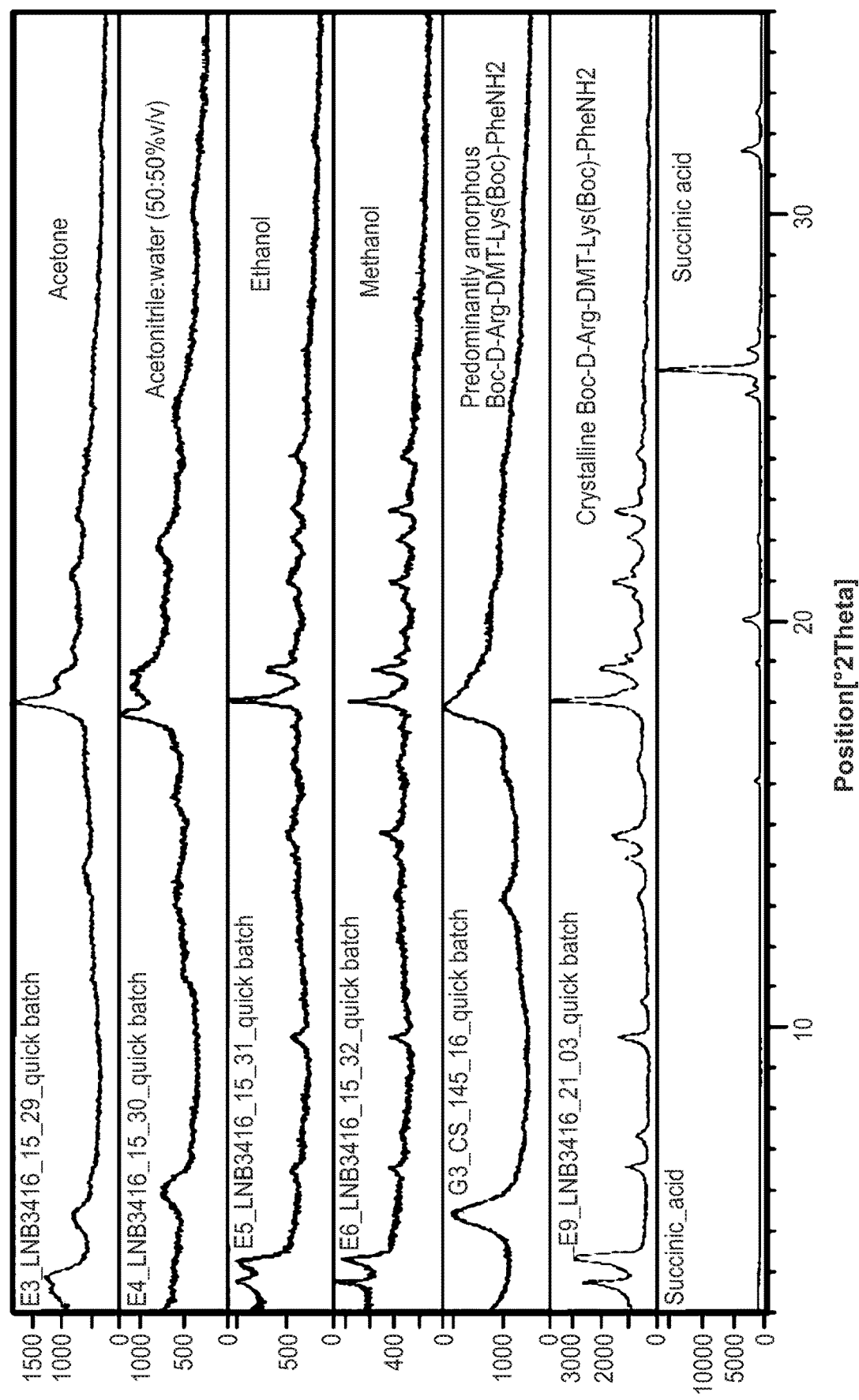
FIG. 8 depicts a XRPD pattern of a succinate salt of Compound I.
Figure 9:
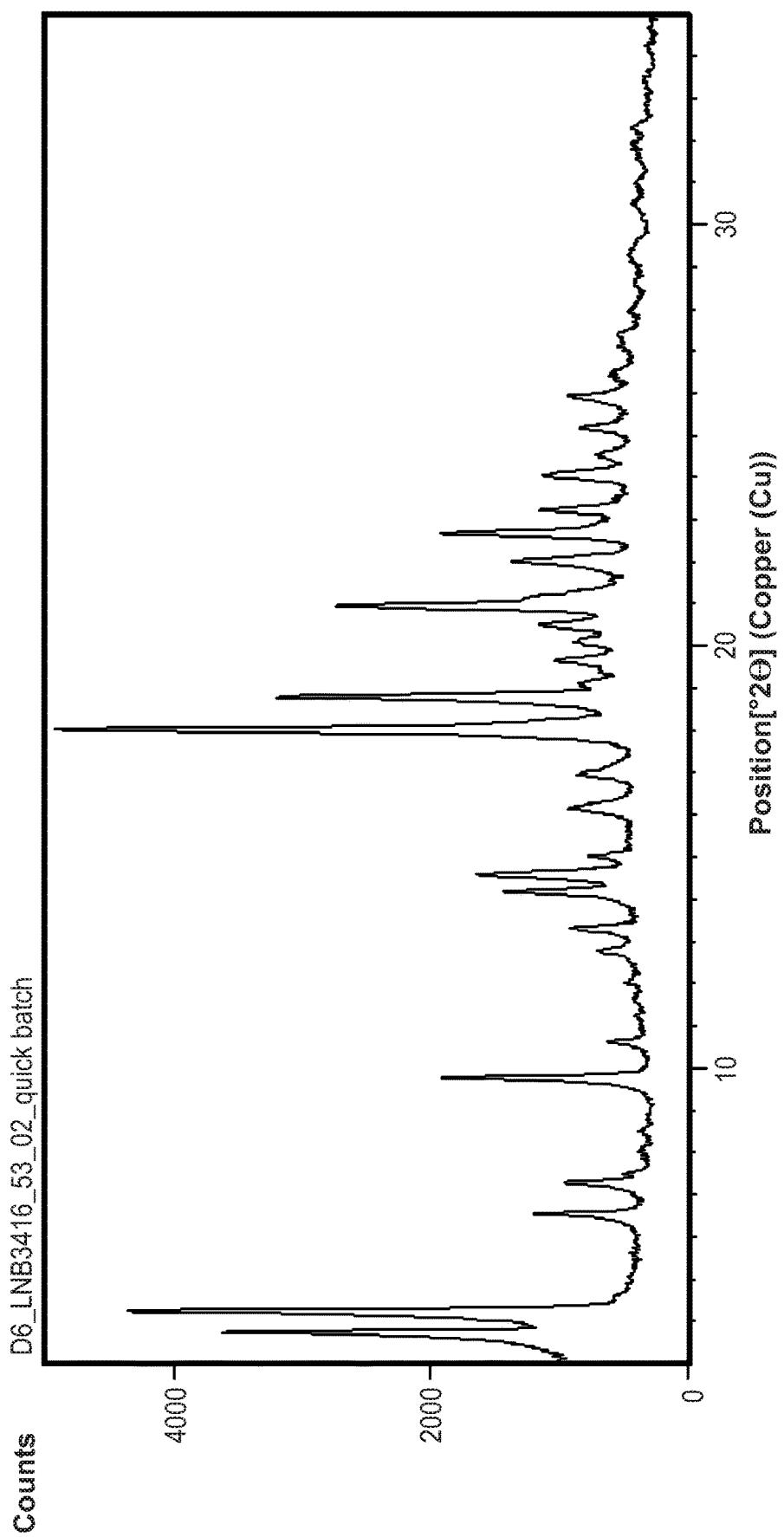
FIG. 9 depicts a XRPD pattern of a hydrochloride salt of Compound I crystallized from Methanol:2-Propanol (75%: 25% v/v).

In another aspect, the invention features a crystalline form of a hydrochloride salt of Compound I, which has characteristic peaks in the X-ray powder diffraction (XRPD) pattern as shown in FIG. 9.

In yet another aspect, the invention features a crystalline form of a hydrochloride salt salt of Compound I, which has characteristic peaks in the X-ray powder diffraction (XRPD) pattern as shown in Table A.

In another aspect, the invention features a crystalline form of a hydrochloride salt of Compound I, which has characteristic peaks in the X-ray powder diffraction (XRPD) pattern at values of two theta (° 2θ) of 3.8, 4.3, 9.8, 14.6, 18.0, 18.8, 20.9, and 22.7.

In another aspect, the invention features a crystalline form of a hydrochloride salt of Compound I, which has characteristic peaks in the X-ray powder diffraction (XRPD) pattern at values of two theta (° 2θ) of 3.8, 4.3, 6.5, 7.3, 9.8, 13.3, 14.2, 14.6, 16.1, 16.9, 18.0, 18.8, 19.1, 19.7, 20.1, 20.5, 20.9, 22.0, 22.7, 23.2, 24.0, 25.2, and 25.9.

Figure 10:
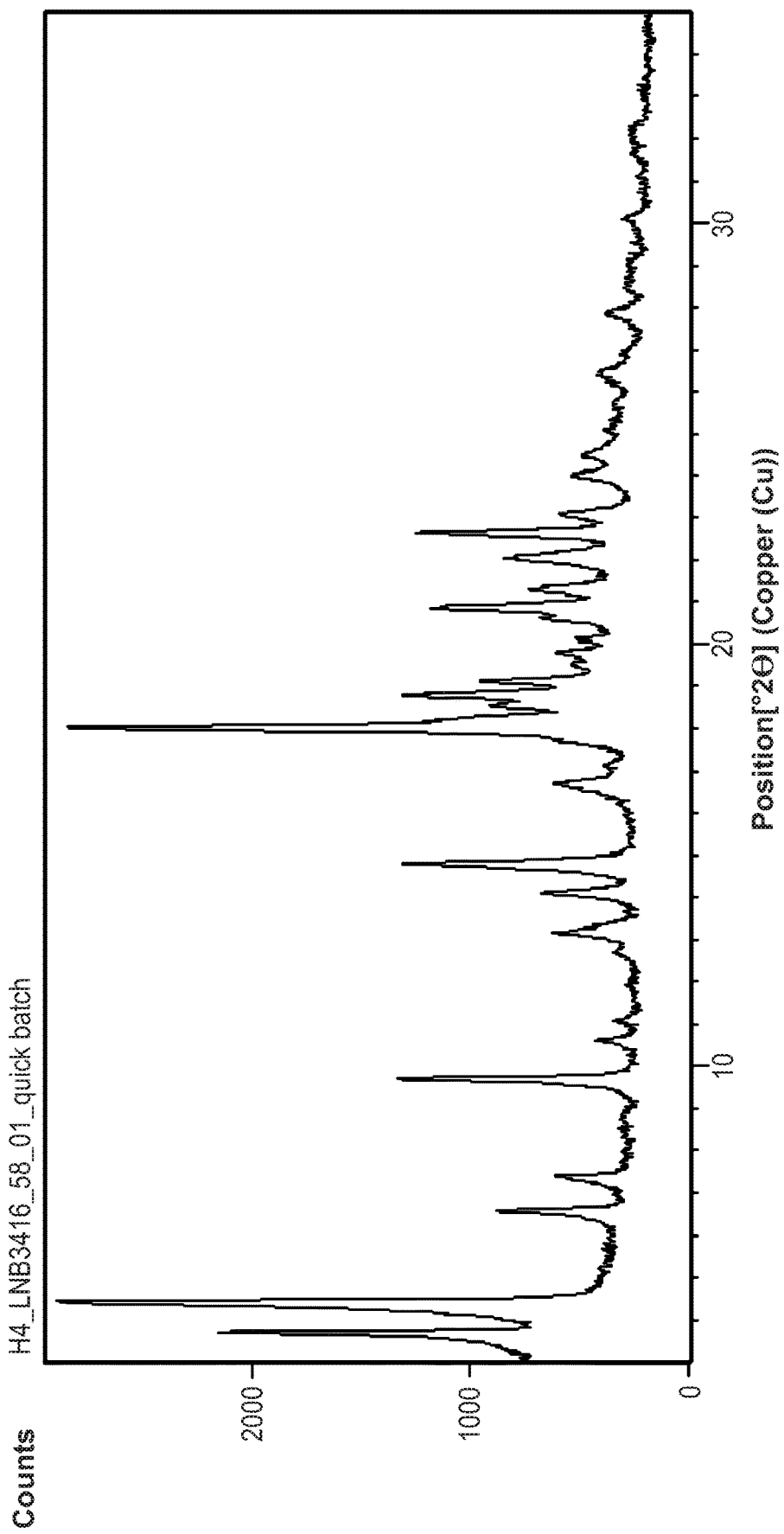
FIG. 10 depicts a XRPD pattern of a hydrochloride salt of Compound I crystallized from Methanol.

In another aspect, the invention features a crystalline form of a hydrochloride salt of Compound I, which has characteristic peaks in the X-ray powder diffraction (XRPD) pattern as shown in FIG. 10.

In yet another aspect, the invention features a crystalline form of a hydrochloride salt salt of Compound I, which has characteristic peaks in the X-ray powder diffraction (XRPD) pattern as shown in Table B.

In another aspect, the invention features a crystalline form of a hydrochloride salt of Compound I, which has characteristic peaks in the X-ray powder diffraction (XRPD) pattern at values of two theta (° 2θ) of 3.7, 4.4, 6.6, 9.7, 14.8, 18.0, 18.5, 18.8, 19.1, 20.9, and 22.7.

In another aspect, the invention features a crystalline form of a hydrochloride salt of Compound I, which has characteristic peaks in the X-ray powder diffraction (XRPD) pattern at values of two theta (° 2θ) of 3.7, 4.4, 6.6, 7.4, 9.7, 10.6, 13.2, 14.1, 14.8, 16.7, 18.0, 18.5, 18.8, 19.1, 19.5, 19.8, 20.1, 20.6, 20.9, 21.3, 22.0, 22.7, 23.1, and 24.0.

Figure 11:
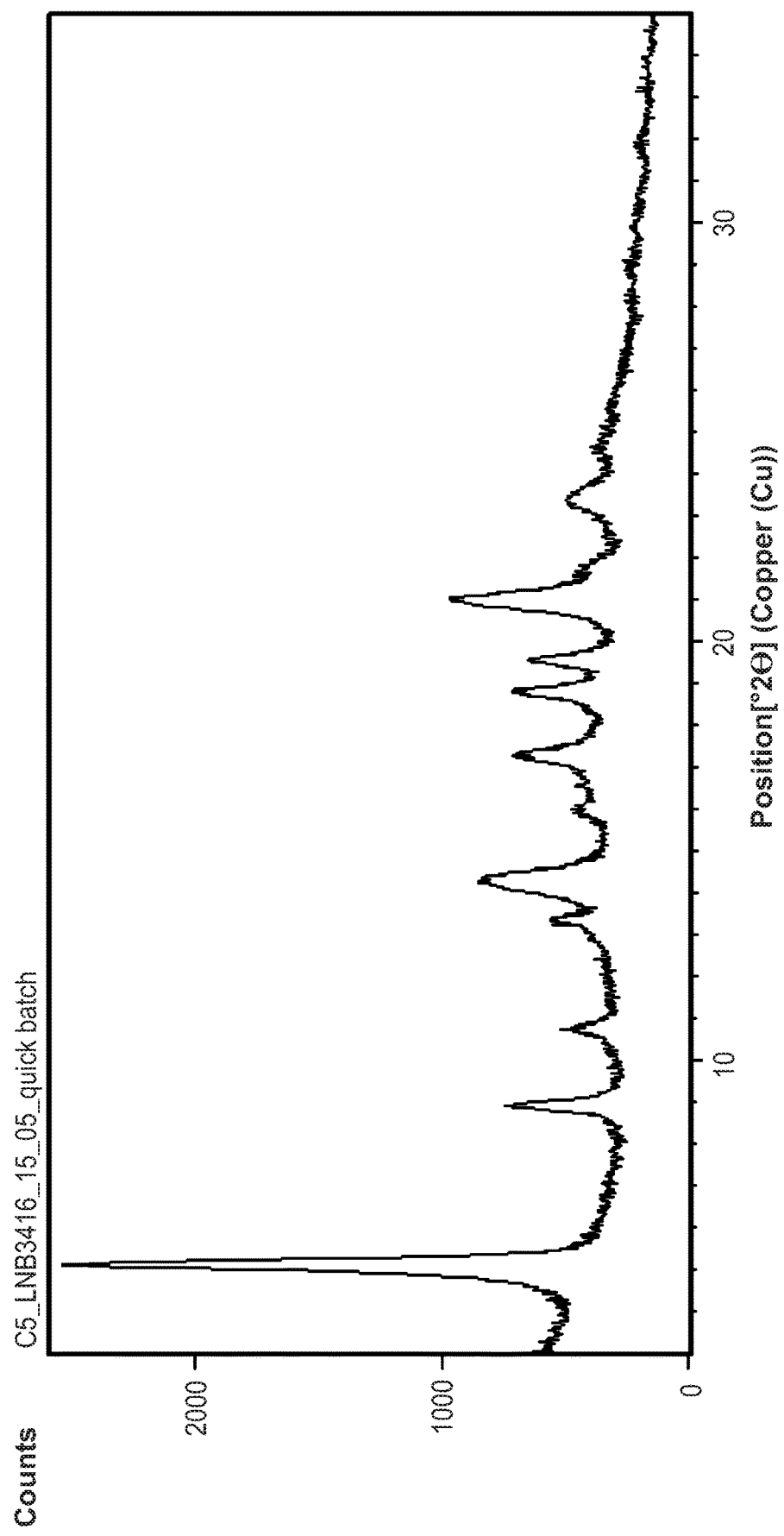
FIG. 11 depicts a XRPD pattern of a tosylate salt of Compound I crystallized from Acetone.

In yet another aspect, the invention features a crystalline form of a tosylate salt of Compound I, which has characteristic peaks in the X-ray powder diffraction (XRPD) pattern as shown in FIG. 11.

In yet another aspect, the invention features a crystalline form of a tosylate salt of Compound I, which has characteristic peaks in the X-ray powder diffraction (XRPD) pattern as shown in Table C.

In another aspect, the invention features a crystalline form of a tosylate salt of Compound I, which has characteristic peaks in the X-ray powder diffraction (XRPD) pattern at values of two theta (° 2θ) of 5.2, 8.9, 14.4, 17.3, 18.8, 19.5, and 21.0.

In another aspect, the invention features a crystalline form of a tosylate salt of Compound I, which has characteristic peaks in the X-ray powder diffraction (XRPD) pattern at values of two theta (° 2θ) of 5.2, 8.9, 10.8, 13.4, 14.4, 16.0, 17.3, 18.8, 19.5, 21.0, 23.3, and 24.6.

Figure 12:
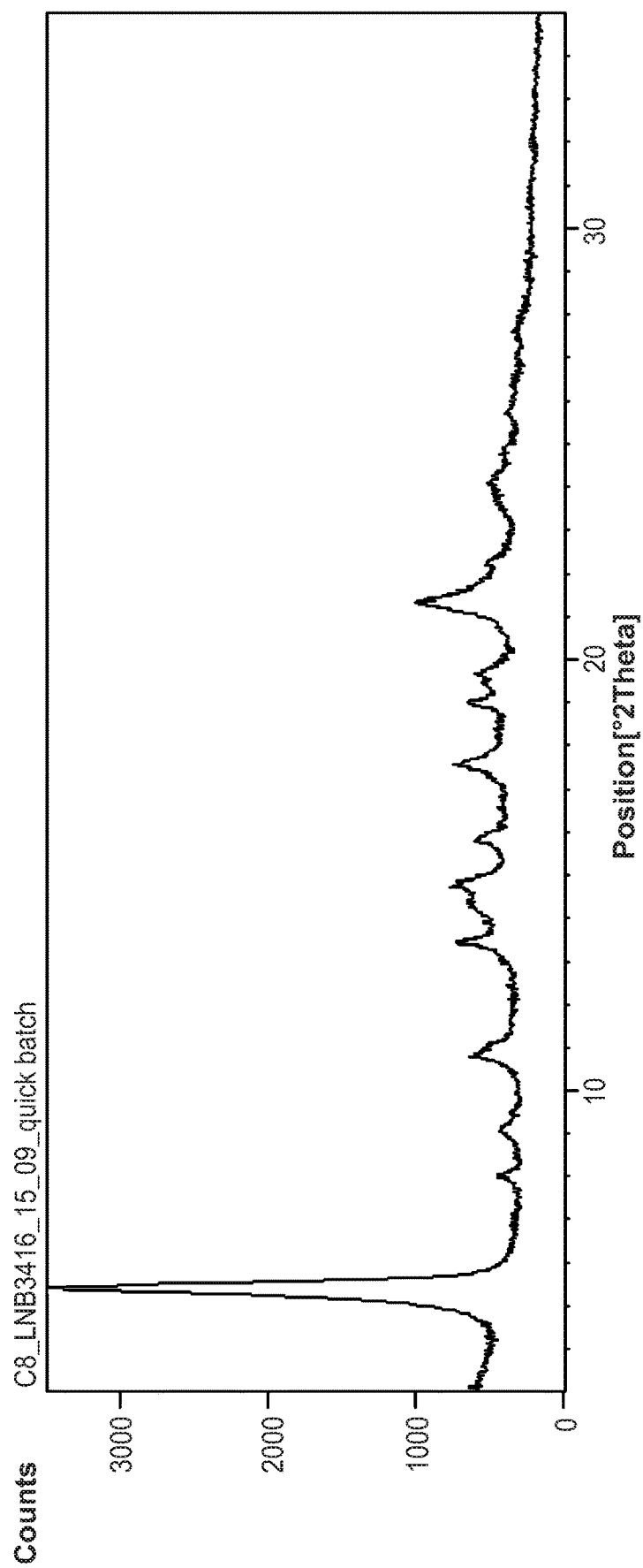
FIG. 12 depicts a XRPD pattern of a mesylate salt of Compound I crystallized from Acetone.

In yet another aspect, the invention features a crystalline form of a mesylate salt of Compound I, which has characteristic peaks in the X-ray powder diffraction (XRPD) pattern as shown in FIG. 12.

In yet another aspect, the invention features a crystalline form of a mesylate salt of Compound I, which has characteristic peaks in the X-ray powder diffraction (XRPD) pattern as shown in Table D.

In another aspect, the invention features a crystalline form of a mesylate salt of Compound I, which has characteristic peaks in the X-ray powder diffraction (XRPD) pattern at values of two theta (° 2θ) of 5.4, 13.4, 14.8, 15.8, 17.6, 19.0, and 21.3.

In another aspect, the invention features a crystalline form of a mesylate salt of Compound I, which has characteristic peaks in the X-ray powder diffraction (XRPD) pattern at values of two theta (° 2θ) of 5.4, 10.8, 13.4, 14.8, 15.8, 17.6, 19.0, 19.7, 21.3, 22.3. 24.1, and 25.7.

Figure 13:
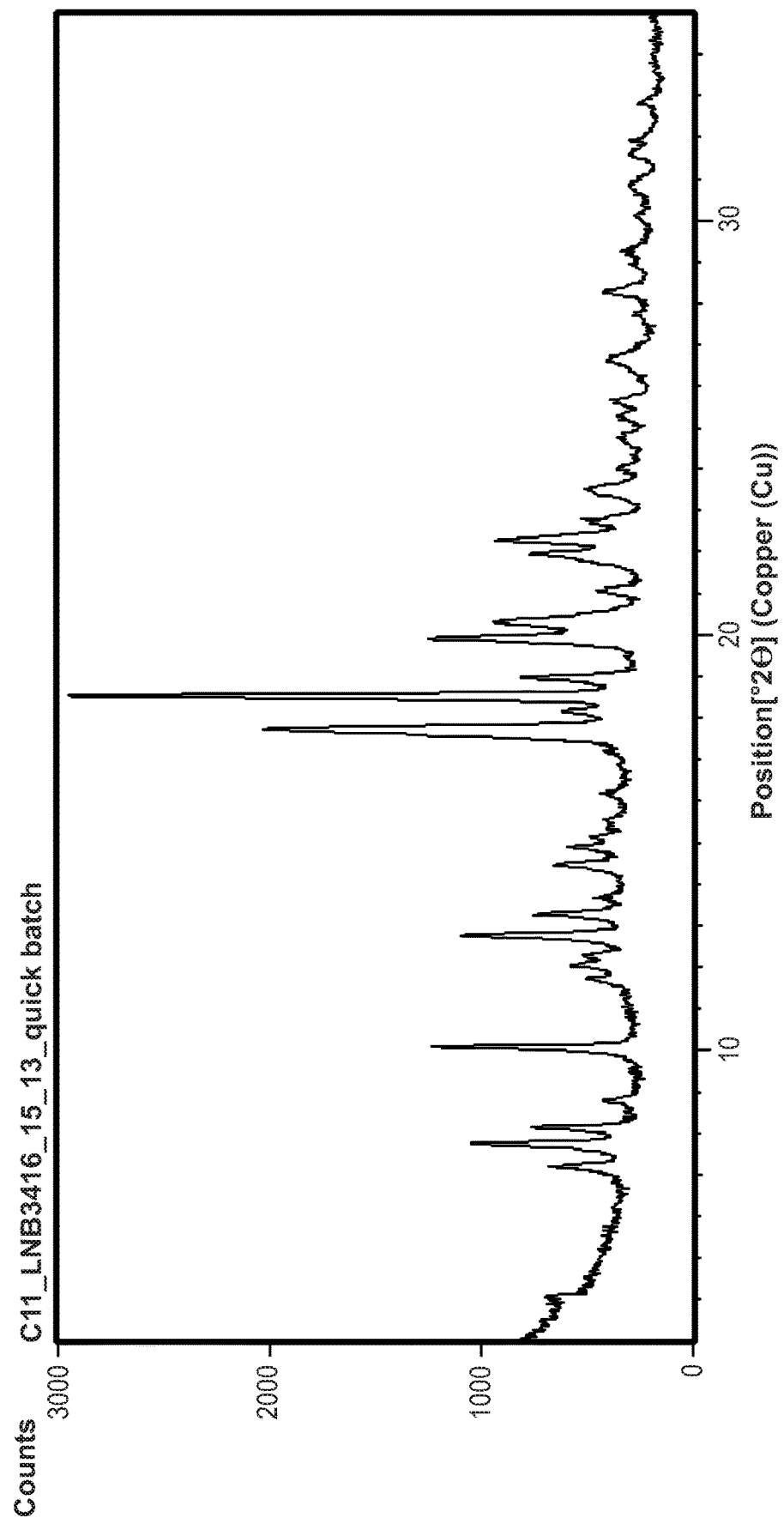
FIG. 13 depicts a XRPD pattern of an oxalate salt of Compound I crystallized from Acetone.

In yet another aspect, the invention features a crystalline form of an oxalate salt of Compound I, which has characteristic peaks in the X-ray powder diffraction (XRPD) pattern as shown in FIG. 13.

In yet another aspect, the invention features a crystalline form of an oxalate salt of Compound I, which has characteristic peaks in the X-ray powder diffraction (XRPD) pattern as shown in Table E.

In another aspect, the invention features a crystalline form of an oxalate salt of Compound I, which has characteristic peaks in the X-ray powder diffraction (XRPD) pattern at values of two theta (° 2θ) of 7.8, 10.1, 12.8, 17.8, 18.5, 19.9, and 22.3.

In another aspect, the invention features a crystalline form of an oxalate salt of Compound I, which has characteristic peaks in the X-ray powder diffraction (XRPD) pattern at values of two theta (° 2θ) of 4.1, 7.2, 7.8, 8.1, 10.1, 12.0, 12.8, 13.3, 14.5, 14.9, 17.8, 18.1. 18.5, 19.9, 20.4, 21.9, 22.0, 22.3, and 23.5.

Figure 14:
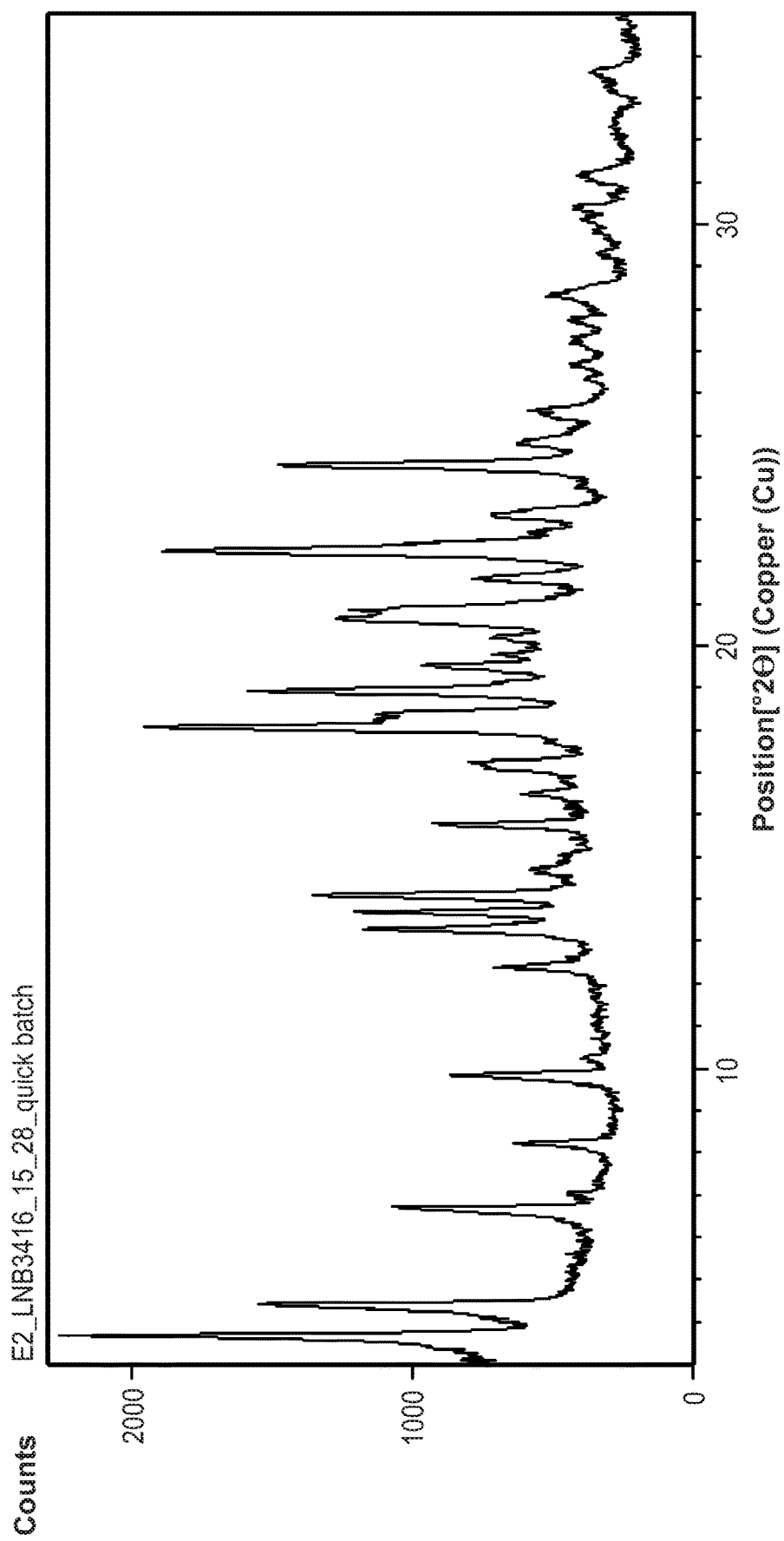
FIG. 14 depicts a XRPD pattern of a benzoate salt of Compound I crystallized from Methanol.

In yet another aspect, the invention features a crystalline form of a benzoate salt of Compound I, which has characteristic peaks in the X-ray powder diffraction (XRPD) pattern as shown in FIG. 14.

In yet another aspect, the invention features a crystalline form of a benzoate salt of Compound I, which has characteristic peaks in the X-ray powder diffraction (XRPD) pattern as shown in Table F.

In another aspect, the invention features a crystalline form of a benzoate of Compound I, which has characteristic peaks in the X-ray powder diffraction (XRPD) pattern at values of two theta (° 2θ) of 3.7, 4.4, 14.1, 18.1, 18.9, 20.7, 22.3, and 24.3.

In another aspect, the invention features a crystalline form of a benzoate salt of Compound I, which has characteristic peaks in the X-ray powder diffraction (XRPD) pattern at values of two theta (° 2θ) of 3.7, 4.4, 6.7, 9.9, 13.3, 13.7, 14.1, 15.8, 17.2, 18.1, 18.4, 18.9, 19.5, 20.7, 20.9, 21.6, 22.3, and 24.3.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

In one embodiment, the present invention features a crystalline form of Compound I which has characteristic peaks in the X-ray powder diffraction (XRPD) pattern as shown in any one of FIGS. 1-8 and which is substantially pure. For example, the crystalline form can be at least 90% pure, preferably at least 95% pure, or more preferably at least 98% pure.

In another embodiment, the present invention features a crystalline form of Compound I which has characteristic peaks in the X-ray powder diffraction (XRPD) pattern at values of two theta (° 2θ) as shown in any one of Tables 1-8 and which is substantially pure. For example, the crystalline form can be at least 90% pure, preferably at least 95% pure, or more preferably at least 98% pure.

In another aspect, the invention relates to preparing compound (II) or a salt thereof (e.g., the tri-HCl salt) from compound (I). In some embodiments, the compound (II) is obtained via deprotection of a crystalline form of compound (I). In some embodiments, the deprotection comprises preparing a mixture (e.g., a slurry) of a crystalline form of compound (I) and a scavenger in a solvent. In some embodiments, the scavenger is triisopropylsilane. In some embodiments the solvent is 2,2,2-trifluoroethanol. In some embodiments, the deprotection further comprises addition of an acid. In some embodiments, the acid is concentrated hydrochloric acid (e.g., 5-6 M HCl).

Methods of Making the Crystalline Salts

In certain embodiments, the invention relates to a method for the preparation of a crystalline salt of compound (I), comprising a) providing a freebase mixture of compound (I) in a first organic solvent; b) contacting the freebase mixture with a reagent solution comprising an acid and optionally a second organic solvent under conditions sufficient to form a mixture comprising a salt of compound (I); and c) crystallizing the salt of compound (I) from the mixture comprising the salt of compound (I).

In certain embodiments, the invention relates to a method for the preparation of a crystalline salt of compound (I), comprising a) providing a first salt mixture of compound (I) in a first organic solvent; b) contacting the first salt mixture with a reagent solution comprising an acid and optionally a second organic solvent under conditions sufficient to form a mixture comprising a second salt of compound (I); and c) crystallizing the second salt of compound (I) from the mixture comprising the second salt of compound (I).

In certain embodiments, the invention relates to a method for the preparation of a crystalline salt of a compound having the structure of formula (II), comprising a) providing a first mixture comprising a protected form of compound (I) in a first organic solvent; b) contacting the first mixture with a reagent solution comprising an acid and optionally a second organic solvent under conditions sufficient to deprotect the protected form of compound (I) and to form a mixture comprising a salt of compound (II); and c) crystallizing the salt of compound (II) from the mixture comprising the salt of compound (II). In certain embodiments, the mixture comprising a salt of compound (I) formed in step b) is a solution. In certain embodiments, the mixture formed in step b) is a slurry or a suspension.

In certain embodiments, the mixture comprising the salt of compound (I) or (II) is a solution, and the step of crystallizing the salt from the mixture comprises bringing the solution to supersaturation to cause the salt of compound (I) or (II) to precipitate out of solution.

In certain embodiments, bringing the mixture comprising the salt of compound (I) or (II) to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the salt of compound (I) or (II) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the salt crystals, e.g. by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise the step of drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, the freebase mixture of compound (I) in a first organic solvent is a slurry. In certain embodiments, the freebase mixture of compound (I) in a first organic solvent is a solution.

In certain embodiments, the first organic solvent and the second organic solvent, if present, comprise acetone, anisole, methanol, 1-butanol, 2-butanone, iso-butanol, tert-butanol, sec-butanol, cyclopentyl methyl ether (CPME), benezotrifluoride (BTF), 1-propanol, 2-propanol (IPA), water, dichloromethane, anisole, acetonitrile, ethylene glycol, tert-butyl methyl ether (t-BME), DMSO, ethylene glycol, toluene, tetrahydrofuran (THF), heptane, acetonitrile, N,N-dimethylacetamide (DMA), dimethylformamide (DMF), dimethylsulfoxide (DMSO), 1,4-dioxane, 2-ethoxy ethanol, heptane, isopropyl acetate, methyl acetate, 2-methyl THF, methyl isobutyl ketone (MIBK), 1-propanol, ethanol, ethyl acetate, hexanes, methyl acetate, isopropyl acetate, methylethyl ketone, 1,4-dioxane, methyl cyclohexane, N-methyl-2-pyrrolidone (NMP), or any combination thereof.

In certain embodiments, the first organic solvent and the second organic solvent, if present, are the same. In alternative embodiments, the first organic solvent and the second organic solvent, if present, are different.

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is ethanol.

In certain embodiments, washing the crystals comprises washing crystalline compound (I) with a solvent or a mixture of one or more solvents, which are described above. In certain embodiments, the solvent or mixture of solvents is cooled prior to washing.

The invention now being generally described, it will be more readily understood by reference to the following examples which are included merely for purposes of illustration of certain aspects and embodiments of the present invention, and are not intended to limit the invention.

EXAMPLES

Materials and Methods
X-Ray Powder Diffraction (XRPD)

Powder x-ray diffraction experiments were performed on a PANalytical X'Pert Pro X-ray Diffractometer, scanning the samples between 3 and 35° 2θ. Material was loaded into a 96-well plate with mylar film as the base. The samples were then loaded into the plate holder of a PANalytical X'Pert Pro X-ray Diffractometer running in transmission mode and analyzed, using the following experimental conditions:

| Raw Data Origin: | XRPD measurement (*.XRPDML) |
|---|---|
| Scan Axis: | Gonio |
| Start Position [°2θ]: | 3.0066 |
| End Position [°2θ]: | 34.9866 |
| Step Size [°2θ]: | 0.0130 |
| Scan Step Time [s]: | 18.8700 |
| Scan Type: | Continuous |
| PSD Mode: | Scanning |
| PSD Length [°2θ]: | 3.35 |
| Offset [°2θ]: | 0.0000 |
| Divergence Slit Type: | Fixed |
| Divergence Slit Size [°]: | 1.0000 |
| Specimen Length [mm]: | 10.00 |
| Measurement Temperature [° C.]: | 25.00 |
| Anode Material: | Cu |
| K-Alpha1 [Å]: | 1.54060 |
| K-Alpha2 [Å]: | 1.54443 |
| K-Beta [Å]: | 1.39225 |
| K-A2/K-A1 Ratio: | 0.50000 |
| Generator Settings: | 40 mA, 40 kV |
| Diffractometer Type: | 0000000011154173 |
| Diffractometer Number: | 0 |
| Goniometer Radius [mm]: | 240.00 |
| Dist. Focus-Diverg. Slit [mm]: | 91.00 |
| Incident Beam Monochromator: | No |
| Spinning: | No |

Polarized Light Microscopy (PLM)

The presence of birefringence was determined using an Olympus BX50 polarizing microscope, equipped with a Motic camera and image capture software (Motic Images Plus 2.0). All images were recorded using the 20× objective, unless otherwise stated.

Thermogravimetric/Differential Thermal Analysis (TG/DTA)

Approximately 5 mg of material was weighed into an open aluminium pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm$^3$/min.

Differential Scanning Calorimetry (DSC)

Approximately 5 mg of material was weighed into an aluminium DSC pan and sealed non-hermetically with a pierced aluminium lid. The sample pan was then loaded into a Seiko DSC6200 (equipped with a cooler) and held at 20° C. Once a stable heat-flow response was obtained, the sample and reference were heated to ca. 180° C. at a scan rate of 10° C./min and the resulting heat flow response monitored. Nitrogen was used as the purge gas, at a flow rate of 50 cm3/min.

Karl Fischer Coulometric Titration (KF)

Approximately 10 mg of solid material was accurately weighed into a vial. The solid was then dissolved in ca. 1 mL or 5 mL of pre-titrated Hydranal solution, sonicating for ca. 5-10 min. The solution was manually introduced into the titration cell of a Mettler Toledo C30 Compact Titrator and the weight of the solid entered on the instrument.

1H Nuclear Magnetic Resonance Spectroscopy (1H NMR)

1H-NMR spectroscopic experiments were performed on a Bruker AV500 (frequency: 500 MHz). Experiments were performed in d6-dimethylsulfoxide and each sample was prepared to ca. 10 mM concentration.

Gravimetric Vapour Sorption (GVS)

Approximately 15 mg of sample was placed into a mesh vapour sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion). After completion of the sorption cycle, the sample was dried using the same procedure to 0% RH, then subjected to a second ramping profile from 0-90% relative humidity. After completion of the second sorption cycle, the sample was dried using the same procedure to 0% RH, and finally taken back to the starting point of 40% RH. The weight change during the sorption/desorption cycles were plotted, allowing for the hygroscopic nature of the sample to be determined.

High Performance Liquid Chromatography-Ultraviolet Detection (HPLC-UV)

Column: *Aeris* Peptide C18 3.6 μm 250×4.6 mm column

Mobile Phase A: 0.05% TFA in deionized water

Mobile Phase B: 0.05% TFA in acetonitrile

Diluent: Water:Acetonitrile (90:10 v/v)

Flow Rate: 1.0 mL/min

Runtime: 32 minutes

Column Temperature: 30° C.

Autosampler Temperature: 5° C.

Injection Volume: 30 μL

Detection: 220 nm

Sample Concentration: 0.5 mg/mL

Gradient program:

| Time/min | Solvent B (%) |
|---|---|
| 0.00 | 5 |
| 15.00 | 25 |
| 20.00 | 50 |
| 25.00 | 90 |
| 27.00 | 90 |
| 27.10 | 5 |
| 32.00 | 5 |

Example 1. Experimental

Approximate Solubility Assessment of Boc-D-Arg-DMT-Lys(Boc)-Phe-NH$_2$

The solubility screen was carried out as follows:

Approximately 20 mg of Boc-D-Arg-DMT-Lys(Boc)-Phe-NH$_2$ was weighed out into each vial.

Each solvent/solvent mixture was added to the appropriate vial in 5 volume aliquots (100 μL).

In between additions, the sample was stirred at 50° C. (35° C. for DCM).

If 2000 μL of solvent was added without dissolution of the material, solubility was calculated to be below this point.

XRPD analysis of residual solids was carried out where solubility was <17 mg/mL.

TABLE 1

| Solvent Systems Selected for Solubility Screen | |
|---|---|
| Solvent | ICH Class |
| Acetone | 3 |
| Ethanol | 3 |
| Methanol | 2 |
| 2-Propanol | 3 |
| 2-Butanol | 3 |
| Methyl ethyl ketone | 3 |
| Dichloromethane* | 2 |
| Toluene | 3 |
| Acetone:water (50:50% v/v) | 3 |
| Ethanol:water (50:50% v/v) | 3 |
| Methanol:water (50:50% v/v) | 2 |
| 2-propanol:water (50:50% v/v) | 3 |
| Tetrahydrofuran | 2 |
| Ethyl acetate | 3 |
| Acetonitrile | 2 |
| Trifluoroethanol | Not classified |
| Acetonitrile:water (50:50% v/v) | 2 |
| DMSO:acetone (50:50% v/v) | 3 |
| DMSO:water (50:50% v/v) | 3 |

Small-Scale Crystallization Trials

Cooling/Temperature Cycling Crystallizations

General Procedure:

ca. 40 mg of Boc-D-Arg-DMT-Lys(Boc)-Phe-NH$_2$ was weighed out into a 2 mL vial.

Respective solvent was added to the appropriate vial at ambient (ca. 22° C.).

The experiments were heated to 50° C. and further stirred at 50° C.

The experiments were stirred at 50° C. for ca. 1 hour.

The experiments were cooled down to 5° C. at 0.1° C./minutes.

The experiments were temperature cycled between 5° C. and 40° C. for about 16 hours of cycling.

For the experiments where a slurry was observed, the solid was isolated by centrifugation using a 0.22 μm Nylon polypropylene centrifuge filter at 5° C. and the isolated material was analyzed by XRPD.

The isolated material was dried under vacuum at ca. 30-40° C. for ca. 18 hours.

TABLE 2

Experimental Details for Small-Scale Cooling/Temperature Cycling Crystallization Trials

| Sample ID | Input Material (mg) | Solvent/solvent system | Vol. of solvent/solvent system used (mL) | Concentration (mg/mL) |
|---|---|---|---|---|
| 1 | 40.07 | Acetone:water (50:50% v/v) | 0.60 | 66.8 |
| 2 | 40.64 | Ethanol | 0.40 | 101.6 |
| 3 | 41.51 | Methanol | 0.28 | 150.4 |
| 4 | 40.13 | Methanol | 0.40 | 100.3 |
| 5 | 41.23 | Trifluoroethanol | 0.10 | 412.3 |
| 6 | 40.40 | Acetonitrile:water (50:50% v/v) | 0.27 | 149.6 |
| 7 | 40.12 | DMSO:water (80:20% v/v) | 0.20 | 200.6 |

Anti-Solvent Addition/Cooling/Temperature Cycling Crystallizations

General Procedure:

ca. 40 mg of Boc-D-Arg-DMT-Lys(Boc)-Phe-NH$_2$ was weighed out into a 2 mL vial.

Respective solvent was added to the appropriate vial at ambient (ca. 22° C.).

The experiments were heated to 50° C. and further stirred at 50° C.

A clear solution was observed at 50° C. for each experiment.

The respective anti-solvent was added to the appropriate experiment at 50° C.

The experiments were stirred at 50° C. for ca. 1 hour.

The experiments were cooled down to 5° C. at 0.1° C./minutes. The experiments were temperature cycled between 5° C. and 40° C. for about 16 hours of cycling.

In the experiments where a thick slurry/thick precipitation was observed, the respective solvent/anti-solvent (same ratio) was added to improve mixing at 5° C.

For the experiments where a slurry was observed, the solid was isolated by centrifugation using a 0.22 μm Nylon polypropylene centrifuge filter at 5° C. and the isolated material was analyzed by XRPD.

TABLE 3

Experimental Details for Anti-solvent addition Cooling/Temperature Cycling Crystallizations

| Sample ID | Input Solid (mg) | Solvent/solvent system | Anti-solvent | Vol. of solvent system used (mL) | Vol. of Anti-solvent used (mL) | Total Volume (mL) | Concentration (mg/mL) | % Solvent | % Anti-Solvent |
|---|---|---|---|---|---|---|---|---|---|
| 1 | 41.63 | Methanol | Acetonitrile | 0.28 | 0.1 | 0.38 | 110.7 | 73.4 | 26.6 |
| 2 | 41.08 | Methanol | EA | 0.28 | 0.1 | 0.38 | 108.1 | 73.7 | 26.3 |
| 3 | 40.92 | Methanol | THF | 0.28 | 0.1 | 0.38 | 107.7 | 73.7 | 26.3 |
| 4 | 40.5 | Methanol | Acetone | 0.28 | 0.1 | 0.38 | 106.6 | 73.7 | 26.3 |
| 5 | 40.15 | Methanol | MEK | 0.28 | 0.1 | 0.38 | 105.7 | 73.7 | 26.3 |
| 6 | 39.99 | Methanol | Toluene | 0.28 | 0.1 | 0.38 | 105.2 | 73.7 | 26.3 |
| 7 | 40.16 | Methanol | Heptane | 0.28 | 0.1 | 0.38 | 105.7 | 73.7 | 26.3 |
| 8 | 41.2 | Ethanol | EA | 0.29 | 0.1 | 0.39 | 105.6 | 74.4 | 25.6 |
| 9 | 41.075 | Ethanol | THF | 0.29 | 0.1 | 0.39 | 105.3 | 74.4 | 25.6 |
| 10 | 42.93 | Ethanol | Acetone | 0.29 | 0.1 | 0.39 | 110.1 | 74.4 | 25.6 |
| 11 | 41.005 | Ethanol | MEK | 0.29 | 0.1 | 0.39 | 105.1 | 74.4 | 25.6 |
| 12 | 40.78 | Ethanol | Toluene | 0.29 | 0.1 | 0.39 | 104.6 | 74.4 | 25.6 |
| 13 | 42.045 | Ethanol | Heptane | 0.29 | 0.1 | 0.39 | 107.8 | 74.4 | 25.6 |
| 14 | 39.295 | Ethanol | TBME | 0.29 | 0.1 | 0.39 | 100.8 | 74.4 | 25.6 |
| 15 | 41.6 | Ethanol | Acetonitrile | 0.29 | 0.1 | 0.39 | 106.7 | 74.4 | 25.6 |
| 16 | 40.16 | Trifluoroethanol | EA | 0.1 | 0.1 | 0.2 | 200.8 | 50.0 | 50.0 |
| 17 | 40.095 | Trifluoroethanol | THF | 0.1 | 0.1 | 0.2 | 200.5 | 50.0 | 50.0 |
| 18 | 42.545 | Trifluoroethanol | Acetone | 0.1 | 0.1 | 0.2 | 212.7 | 50.0 | 50.0 |
| 19 | 41.175 | Trifluoroethanol | MEK | 0.1 | 0.1 | 0.2 | 205.9 | 50.0 | 50.0 |
| 20 | 41.365 | Trifluoroethanol | Toluene | 0.1 | 0.1 | 0.2 | 206.8 | 50.0 | 50.0 |
| 21 | 39 | Trifluoroethanol | Heptane | 0.1 | 0.1 | 0.2 | 195.0 | 50.0 | 50.0 |
| 22 | 40.2 | Trifluoroethanol | TBME | 0.1 | 0.1 | 0.2 | 201.0 | 50.0 | 50.0 |
| 23 | 41.48 | Trifluoroethanol | Acetonitrile | 0.1 | 0.1 | 0.2 | 207.4 | 50.0 | 50.0 |

Anti-Solvent Addition Crystallizations
General Procedure:

ca. 40 mg of Boc-D-Arg-DMT-Lys(Boc)-Phe-NH$_2$ was weighed out into a 2 mL vial.

Respective solvent was added to the appropriate vial at ambient (ca. 22° C.).

The experiments were heated to 50° C. and stirred at 50° C.

Clear solution was observed at 50° C. for each experiment.

For addition of anti-solvent at 5° C.:
  The experiments were cooled down to 5° C. at 0.1° C./minutes and temperature cycled between 5° C. to 40° C. at 0.1° C./minutes for ca. 18 hours cycle.
  At 5° C., respective anti-solvent was added to the appropriate experiment.
  Further the experiments were stirred at 5° C. for ca 2 hours.

For anti-solvent addition at 50° C.:
  To the clear solutions at 50° C., respective anti-solvents were added.
  The experiments were stirred at 50° C. for ca. 2 hours.
  The experiments were cooled down to 5° C. at 0.1° C./minutes. The experiments were temperature cycled between 5° C. and 40° C. for about 18 hour cycles.

In the experiments where a thick slurry/thick precipitation was observed, the respective solvent/anti-solvent (same ratio) was added to ensure a stirrable slurry at 5° C.

For the experiments where a flowable slurry was observed, the solid was isolated by centrifugation using 0.22 μm Nylon polypropylene centrifuge tube at 5° C. and the isolated material was analyzed by XRPD.

The isolated material was dried under vacuum at 40° C. for ca. 24 hours.

TABLE 4

Experiment Details for Anti-Solvent Addition Crystallizations

| Sample ID | Input Material (mg) | Solvent/solvent system | Anti-solvent | Temperature | Vol. of solvent system used (mL) | Vol. of Anti-solvent used (mL) | Total Volume (mL) | Concentration (mg/mL) | % Solvent | % Anti-Solvent |
|---|---|---|---|---|---|---|---|---|---|---|
| 1 | 39.83 | Methanol | Acetonitrile | 50° C. | 0.27 | 0.81 | 1.08 | 36.9 | 25 | 75 |
| 2 | 39.61 | | EA | | 0.27 | 0.81 | 1.08 | 36.7 | 25 | 75 |
| 3 | 39.48 | | THE | | 0.27 | 0.81 | 1.08 | 36.6 | 25 | 75 |
| 4 | 40.49 | | Acetone | | 0.27 | 0.81 | 1.08 | 37.5 | 25 | 75 |
| 5 | 39.8 | | MEK | | 0.27 | 0.81 | 1.08 | 36.9 | 25 | 75 |
| 6 | 40.35 | | Toluene | | 0.27 | 0.81 | 1.08 | 37.4 | 25 | 75 |
| 7 | 40.53 | | TBME | | 0.27 | 0.81 | 1.08 | 37.5 | 25 | 75 |
| 8 | 39.51 | Ethanol | Acetonitrile | 50° C. | 0.29 | 0.87 | 1.16 | 34.1 | 25 | 75 |
| 9 | 41.04 | | EA | | 0.29 | 0.87 | 1.16 | 35.4 | 25 | 75 |
| 10 | 41.18 | | THE | | 0.29 | 0.87 | 1.16 | 35.5 | 25 | 75 |
| 11 | 42.05 | | Acetone | | 0.29 | 0.87 | 1.16 | 36.3 | 25 | 75 |
| 12 | 40.1 | | MEK | | 0.29 | 0.87 | 1.16 | 34.6 | 25 | 75 |

TABLE 4-continued

Experiment Details for Anti-Solvent Addition Crystallizations

| Sample ID | Input Material (mg) | Solvent/ solvent system | Anti-solvent | Temperature | Vol. of solvent system used (mL) | Vol. of Anti-solvent used (mL) | Total Volume (mL) | Concentration (mg/mL) | % Solvent | % Anti-Solvent |
|---|---|---|---|---|---|---|---|---|---|---|
| 13 | 41.31 | | Toluene | | 0.29 | 0.87 | 1.16 | 35.6 | 25 | 75 |
| 14 | 41.27 | | TBME | | 0.29 | 0.87 | 1.16 | 35.6 | 25 | 75 |
| 15 | 39.7 | | Heptane | | 0.29 | 0.87 | 1.16 | 34.2 | 25 | 75 |
| 16 | 40.69 | Methanol | Acetonitrile | 5° C. | 0.27 | 0.81 | 1.08 | 37.7 | 25 | 75 |
| 17 | 40.82 | | EA | | 0.27 | 0.81 | 1.08 | 37.8 | 25 | 75 |
| 18 | 41.28 | | THF | | 0.27 | 0.81 | 1.08 | 38.2 | 25 | 75 |
| 19 | 40.29 | | Acetone | | 0.27 | 0.81 | 1.08 | 37.3 | 25 | 75 |
| 20 | 39 35 | | MEK | | 0.27 | 0.81 | 1.08 | 36.4 | 25 | 75 |
| 21 | 40.74 | | Toluene | | 0.27 | 0.81 | 1.08 | 37.7 | 25 | 75 |
| 22 | 41.68 | | TBME | | 0.27 | 0.81 | 1.08 | 38.6 | 25 | 75 |
| 23 | 40.96 | Ethanol | Acetonitrile | 5° C. | 0.29 | 0.87 | 1.16 | 35.3 | 25 | 75 |
| 24 | 40.33 | | EA | | 0.29 | 0.87 | 1.16 | 34.8 | 25 | 75 |
| 25 | 41.12 | | THF | | 0.29 | 0.87 | 1.16 | 35.4 | 25 | 75 |
| 26 | 39.97 | | Acetone | | 0.29 | 0.87 | 1.16 | 34.5 | 25 | 75 |
| 27 | 40.31 | | MEK | | 0.29 | 0.87 | 1.16 | 34.7 | 25 | 75 |
| 28 | 40.85 | | Toluene | | 0.29 | 0.87 | 1.16 | 35.2 | 25 | 75 |
| 29 | 40.72 | | TBME | | 0.29 | 0.87 | 1.16 | 35.1 | 25 | 75 |
| 30 | 39.7 | | Heptane | | 0.29 | 0.87 | 1.16 | 34.2 | 25 | 75 |

Seeded Cooling Crystallizations using Solvent/Anti-Solvent Mixtures

General Procedure:
ca. 40 mg of Boc-D-Arg-DMT-Lys(Boc)-Phe-NH$_2$ was weighed out into a 2 mL vial.

Respective solvent was added to the appropriate vial at ambient.

The experiments were heated to 50° C. and further stirred at 50° C.

A clear solution was observed at 50° C. for each experiment.

The respective anti-solvent was added to the appropriate experiment at 50° C. Clear solution was observed. The experiments were seeded using crystalline Form 1.

Seed persisted in all the crystallizations and turbidity was observed.

The experiments were stirred at 50° C. for ca. 1 hour.

Further nucleation was observed in every experiment.

The experiments were cooled down to 5° C. at 0.1° C./minute. The experiments were further stirred at 5° C.

In the experiments where a thick slurry/thick precipitation was observed, the respective solvent/anti-solvent (same ratio) was added to improve mixing at 5° C.

The experiments were isolated by centrifugation using a 0.22 μm Nylon polypropylene centrifuge filter at 5° C. and the isolated material was analyzed by XRPD.

Dried under vacuum at 35° C. to 40° C. for ca. 24 hours.

TABLE 5

Experimental Details for Seeded Cooling Crystallizations using Solvent/Anti-solvent Mixtures

| Sample ID | Input material (mg) | Solvent | Anti-solvent | Vol. of solvent used (mL) | Vol. of Anti-solvent used (mL) | Total Volume (mL) | Concentration (mg/mL) | % Solvent | % anti-solvent/ co-solvent |
|---|---|---|---|---|---|---|---|---|---|
| 1 | 40.3 | Methanol | Acetone | 0.27 | 0.090 | 0.360 | 111.9 | 75 | 25 |
| 2 | 40 | Methanol | 2-propanol | 0.27 | 0.090 | 0.360 | 111.1 | 75 | 25 |
| 3 | 39.9 | Methanol | 2-butanol | 0.27 | 0.090 | 0.360 | 110.8 | 75 | 25 |
| 4 | 41.5 | Methanol | TBME | 0.27 | 0.090 | 0.360 | 115.3 | 75 | 25 |
| 5 | 42.05 | Methanol | Ethanol | 0.20 | 0.200 | 0.400 | 105.1 | 50 | 50 |
| 6 | 41.5 | Ethanol | 2-propanol | 0.29 | 0.097 | 0.387 | 107.3 | 75 | 25 |
| 7 | 39.9 | Ethanol | 2-butanol | 0.29 | 0.097 | 0.387 | 103.2 | 75 | 25 |

Scale-up Seeded Cooling Crystallizations Using Solvent/Anti-Solvent Mixture

In order to reproduce the most promising small-scale crystallizations, to assess repeatability and obtain further material for characterization, scale-up crystallizations were carried out. The following procedure was used:

ca. 250 mg of Boc-D-Arg-DMT-Lys(Boc)-Phe-NH$_2$ was weighed out into a 20 mL scintillation vial.

Respective solvent was added to the appropriate vial at ambient.

The experiments were heated to 50° C. and further stirred at 50° C.

A clear solution was observed at 50° C. for each experiment.

The respective anti-solvent was added to the appropriate experiment at 50° C. Clear solution was observed. The experiments were seeded using crystalline Form 1.

Seed persisted in all the crystallizations and turbidity was observed.

The experiments were stirred at 50° C. for ca. 1 hour. Further nucleation was observed in every experiment.

The experiments were cooled down to 5° C. at 0.1° C./minutes. The experiments were further stirred at 5° C.

The experiments were isolated at 5° C. by filtering over a Buchner funnel using Whatmann filter paper (Grade 597).

The isolated material from each batch was air dried for ca. 18 hours and further dried under vacuum at 35° C. to 40° C. for ca. 24 hours.

TABLE 6

Experimental Details for Scale-up Seeded Cooling Crystallizations

| Sample ID | Input material (mg) | Solvent | Anti-solvent | Concentration in solvent (mg/mL) | Vol. of solvent used (mL) | Vol. of Anti-solvent used (mL) | Total Volume (mL) | Concentration after ASA (mg/mL) | % Solvent | % Anti-solvent |
|---|---|---|---|---|---|---|---|---|---|---|
| 1 | 254 | Methanol | | 100 | 2.543 | | 2.543 | 100.00 | 100 | |
| 2 | 250 | Methanol | Acetonitrile | 150 | 1.667 | 0.556 | 2.222 | 112.50 | 75 | 25 |
| 3 | 256 | Methanol | THF | 150 | 1.708 | 5.125 | 6.834 | 37.50 | 25 | 75 |
| 4 | 252 | Ethanol | Acetone | 140 | 1.804 | 5.412 | 7.216 | 35.00 | 25 | 75 |

Primary Salt Screening

General Procedure ca. 25 mg of Boc-D-Arg-DMT-Lys(Boc)-Phe-$NH_2$ was weighed out into a 2 mL vial.

Respective solvent was added to the appropriate vial at ambient.

The experiments were stirred at 50° C. for ca. 1 hour.
  For experiments using acetone as a solvent, a slurry was observed.
  For all other solvents, initially clear solutions were observed but during further stirring at 50° C. precipitation were observed. A slurry was present.

Further respective solvent was added to the appropriate experiments either to dissolve the precipitated material or to improve stirring.

The counterions were weighed (1.0 mole equivalent). To the vials containing counterion, the respective solvent was added at ambient.

The solution/slurry of counterion in the respective solvent system was added to the appropriate vial containing the slurry/clear solution of Boc-D-Arg-DMT-Lys(Boc)-Phe-$NH_2$ in the respective solvent system at 50° C.

The vial containing solution/slurry of counterion was washed with the respective solvent (50 μL) and the washings were added to the salt formation reaction.

The experiments were stirred at 50° C. for ca. 1 hour.

In the experiments where a thick slurry was observed, the respective solvent was added to improve mixing.

The experiments were cooled down to 5° C. at 0.1° C./minutes. The experiments were temperature cycled between 5° C. and 40° C. for ca. 16 hours of cycling.

At 16 hours, observations were recorded.
  Temperature cycling was continued for a total of ca. 40 hours.
  For the experiments where a slurry was observed, the solid was isolated by centrifugation using a 0.22 μm Nylon polypropylene centrifuge filter at 5° C.
    The isolated material was dried under vacuum at 30° C. for 2 hours.
  The isolated material was analyzed by XRPD.

TABLE 7

Experimental Details for Primary Salt Screening

| Sample ID | Mass of Input Material (mg) | Solvent/ solvent system | Counterion | Mass of counterion (mg or μL) | Solvent system added to input material (μL) | Initial concentration (mg/mL) | Further solvent system added either to dissolve or to make slurry (μL) | Solvent system for counterion (μL) | Further solvent system added to improve mixing (μL) |
|---|---|---|---|---|---|---|---|---|---|
| 1 | 26.26 | Acetone | HCl | 2.7 | 600 | 43.77 | N/A | 75 | 100 |
| 2 | 25.5 | Acetonitrile:water (50:50% v/v) | | 2.6 | 130 | 196.15 | 25 | 50 | 100 |
| 3 | 26.18 | Ethanol | | 2.6 | 187 | 140.00 | 50 | 50 | N/A |
| 4 | 26.53 | Methanol | | 2.7 | 132 | 200.98 | 75 | 50 | N/A |
| 5 | 25.38 | Acetone | P-toluene sulfonic acid | 5.93 | 400 | 63.45 | N/A | 75 | N/A |
| 6 | 25.23 | Acetonitrile:water (50:50% v/v) | | 5.97 | 130 | 194.08 | 25 | 50 | N/A |
| 7 | 25.33 | Ethanol | | 6.06 | 187 | 135.45 | 50 | 50 | N/A |
| 8 | 25.53 | Methanol | | 5.99 | 132 | 193.41 | 75 | 50 | N/A |
| 9 | 26.04 | Acetone | Methane sulfonic acid | 2 | 400 | 65.10 | N/A | 75 | N/A |
| 10 | 25.5 | Acetonitrile:water (50:50% v/v) | | 2 | 130 | 196.15 | 25 | 50 | N/A |
| 11 | 26.04 | Ethanol | | 2 | 187 | 139.25 | 50 | 50 | N/A |
| 12 | 26.44 | Methanol | | 2.1 | 132 | 200.30 | 75 | 50 | N/A |
| 13 | 25.74 | Acetone | Oxalic acid | 2.95 | 400 | 64.35 | N/A | 75 | N/A |
| 14 | 26.18 | Acetonitrile:water (50:50% v/v) | | 2.99 | 130 | 201.38 | 25 | 50 | N/A |
| 15 | 26.61 | Ethanol | | 2.98 | 187 | 142.30 | 50 | 50 | N/A |
| 16 | 25.81 | Methanol | | 2.86 | 132 | 195.53 | 75 | 50 | N/A |

TABLE 8

Experimental Details for Primary Salt Screening

| Sample ID | Mass of Input material (mg) | Solvent/ solvent system | Counter-ion | Mass of counter-ion (mg or μL) | Solvent system added to input material (μL) | Initial concentration (mg/mL) | Further solvent system added either to dissolve or to make slurry (μL) | Solvent system for counter-ion (μL) | Further solvent system added to improve mixing (μL) |
|---|---|---|---|---|---|---|---|---|---|
| 17 | 25.36 | Acetone | L-Tartaric acid | 4.69 | 400 | 63.40 | N/A | 75 | N/A |
| 18 | 26.29 | Acetonitrile:water (50:50%)v/v | | 4.87 | 130 | 202.23 | 25 | 50 | 100 |
| 19 | 25.05 | Ethanol | | 4.66 | 187 | 133.96 | 50 | 50 | 100 |
| 20 | 25.4 | Methanol | | 4.8 | 132 | 192.42 | 75 | 50 | 100 |
| 21 | 26.2 | Acetone | Fumaric Acid | 3.96 | 400 | 65.50 | NA | 75 | N/A |
| 22 | 25.26 | Acetonitrile:water (50:50%)v/v | | 3.67 | 130 | 194.31 | 25 | 50 | N/A |
| 23 | 25.22 | Ethanol | | 3.69 | 187 | 134.87 | 50 | 50 | N/A |
| 24 | 25.34 | Methanol | | 3.62 | 132 | 191.97 | 75 | 50 | N/A |
| 25 | 26 | Acetone | Benzoic acid | 3.88 | 400 | 65.00 | N/A | 75 | 100 |
| 28 | 26.49 | Acetonitrile:water (50:50%)v/v | | 4.09 | 130 | 203.77 | 25 | 50 | N/A |
| 27 | 25.27 | Ethanol | | 3.78 | 187 | 135.13 | 50 | 50 | N/A |
| 28 | 25.23 | Methanol | | 3.86 | 132 | 191.14 | 75 | 50 | N/A |

TABLE 8-continued

Experimental Details for Primary Salt Screening

| Sample ID | Mass of Input material (mg) | Solvent/ solvent system | Counter-ion | Mass of counter-ion (mg or μL) | Solvent system added to input material (μL) | Initial concentration (mg/mL) | Further solvent system added either to dissolve or to make slurry (μL) | Solvent system for counter-ion (μL) | Further solvent system added to improve mixing (μL) |
|---|---|---|---|---|---|---|---|---|---|
| 29 | 25.2 | Acetone | Succinic acid | 3.67 | 400 | 63.00 | N/A | 75 | 100 |
| 30 | 25.75 | Acetonitrile:water (50:50%)v/v | | 3.86 | 130 | 198.08 | 25 | 50 | N/A |
| 31 | 25.24 | Ethanol | | 3.61 | 187 | 134.97 | 50 | 50 | 100 |
| 32 | 26.43 | Methanol | | 3.88 | 132 | 203.23 | 75 | 50 | N/A |

Example 2. Results

Characterization of Boc-D-Arg-DMT-Lys(Boc)-Phe-NH$_2$ by XRPD, PLM, TG/DTA, DSC, GVS, KF and HPLC-UV.
Characteristics:
  predominantly amorphous by XRPD analysis.
  non-birefringent by PLM analysis, with no clearly defined morphology.
  TG analysis showed a weight loss of ca. 2.79% from the outset up to ca. 144° C., followed by weight loss of ca. 0.72% corresponding to an endothermic event in the DTA at an onset of ca. 144.3° C. (peak at ca. 155.2° C.).
  DSC analysis showed a broad endothermic event from the outset up to ca. 140° C., likely due to unbound solvent/water. A second endotherm was observed at an onset of ca. 140.2° C. (peak at 155.6° C.).
  GVS analysis of the indicated that Boc-D-Arg-DMT-Lys(Boc)-Phe-NH$_2$, is highly hygroscopic, with a mass increase of ca. 10% between 40-90% RH observed. The post-GVS sample was also found to be predominantly amorphous by XRPD.
  contained ca. 3.61% water by KF analysis.
  purity of 97.50% by HPLC analysis.
Approximate Solubility Assessment of Boc-D-Arg-DMT-Lys(Boc)-Phe-NH$_2$
The solubility assessment was estimated by a solvent addition technique, heating at 50° C. between aliquots (see Table 9). The following observations and results were obtained:
  excellent solubility in methanol, trifluoroethanol, acetonitrile:water (50:50% v/v) and DMSO:acetone (50:50% v/v) giving solubility values of ≥200 mg/mL.
  Solubility values of ca. 140 mg/mL in ethanol and ca. 100 mg/mL in 2-propanol:water (50:50% v/v) and ethanol:water (50:50% v/v) were also observed.
  Moderate solubility (ca. 58 to 24 mg/mL) was obtained in acetone:water (50:50 v/v), methanol:water (50:50 v/v), and DMSO:water (50:50 v/v).
  Poor solubility (≤17 mg/mL) was obtained in all other solvent systems investigated, including acetone, dichloromethane, 2-butanol, 2-propanol, methyl ethyl ketone, toluene, THF, ethyl acetate and acetonitrile.
  XRPD analysis was carried out on residual solids from some of the solvent systems showing poor solubility, after slurrying at 50° C. overnight, with diffractograms of residual solids being predominantly amorphous.

TABLE 9

Approximate Solubility Screen Results

| Solvent | Approximate Solubility (50° C.)/mg/mL |
|---|---|
| Acetone | <10 |
| Ethanol | 140 |
| Methanol | 200 |
| 2-Propanol | 14 |
| 2-Butanol | 17 |
| Methyl ethyl ketone | <10 |
| Dichloromethane* | <10 |
| Toluene | <10 |
| Acetone:water (50:50% v/v) | 58 |
| Ethanol:water (50:50% v/v) | 100 |
| Methanol:water (50:50% v/v) | 45 |
| 2-propanol:water (50:50% v/v) | 100 |
| Tetrahydrofuran | <10 |
| Ethyl acetate | <10 |
| Acetonitrile | <10 |
| Trifluoroethanol | >200 |
| Acetonitrile:water (50:50% v/v) | 200 |
| DMSO:acetone (50:50% v/v) | 400 |
| DMSO:water (50:50% v/v) | 24 |

*35° C. for dichloromethane

Small-Scale Crystallization Trials
Cooling/Temperature Cycling Crystallizations
Small-scale temperature cycling crystallization trials using Boc-D-Arg-DMT-Lys(Boc)-Phe-NH$_2$ were carried out in 7 different solvent systems, using ethanol, methanol, trifluoroethanol, acetone:water (50:50% v/v, Acetonitrile:water(50:50% v/v) and DMSO:water (80;20% v/v). The following results and observations were obtained from these experiments:
  Clear solutions were observed in all of the experiments at 50° C.
  Within 1 hour of granulation at 50° C., nucleation followed by crystallization was observed in experiments using methanol at both concentrations of ca. 100 mg/mL and 150 mg/mL.
  Observations and results are summarized in Table 10.
  XRPD analysis showed crystallization of the material from experiments using methanol as a solvent.
  PLM analysis of the dried, crystalline solids from methanol (ca. 100 mg/mL and 150 mg/mL concentration) indicated that the material was birefringent with no well-defined morphology.
  TG/DT analysis of the dried material isolated from methanol (100 mg/mL) showed a weight loss of ca.1.39% from the outset up to ca. 168° C. An endothermic event at an onset of 168.5° C. (peak at 175.9° C.) followed by degradation of the material was observed in the DTA.

HPLC analysis of the dried material isolated from acetone: water (50:50% v/v) and ethanol indicated a purity value of 98.80% and 98.81% respectively.

HPLC analysis of the dried crystalline material isolated from methanol using concentrations of ca. 150 mg/mL and ca. 100 mg/mL indicated purity values of 98.24% and 98.62% respectively.

TABLE 10

Observations and Results from Cooling/Temperature Cycling Crystallizations

| Sample ID | Solvent/solvent system | Observation at 50° C. | Observation after temperature cycling | XRPD |
|---|---|---|---|---|
| 1 | Acetone:water (50:50% v/v) | Clear solution | Slurry | Predominantly amorphous |
| 2 | Ethanol | Clear solution | Gel-like | Predominantly amorphous |
| 3 | Methanol | Clear solution | Very thick slurry | Crystalline |
| 4 | Methanol | Clear solution | Slurry | Crystalline |
| 5 | Trifluoroethanol | Clear solution | Clear solution | |
| 6 | Acetonitrile:water (50:50% v/v) | Clear solution | Gel-like thin slurry | |
| 7 | DMSO:water (80:20% v/v) | Clear solution | Clear solution | |

Anti-Solvent Addition/Cooling/Temperature Cycling Crystallizations

Small-scale cooling followed temperature cycling produced crystalline material using methanol as a solvent. In order to investigate further solvent systems for crystallization of Boc-D-Arg-DMT-Lys(Boc)-Phe-NH$_2$, cooling/temperature cycling crystallizations were carried out using methanol, ethanol and trifluoroethanol as the solvents and using acetonitrile, ethyl acetate, THF, acetone, MEK, toluene and heptane as the anti-solvents. The following results and observations were obtained from these experiments:

After temperature cycling, a slurry was observed for experiments using methanol/anti-solvent mixtures.

Thick precipitation was observed after temperature cycling for most of the experiments using ethanol/anti-solvent and trifluoroethanol/anti-solvent mixtures.

The wet material isolated from methanol/anti-solvent mixtures was free flowing but the wet material from ethanol/anti-solvents and trifluoroethanol/anti-solvents was gel-like.

Observations and results are summarized in Table 11 and Table 12 respectively.

XRPD analysis on the isolated material indicated that crystalline material was produced from methanol/anti-solvent mixtures and poorly crystalline to partially crystalline material from ethanol/anti-solvent mixtures and trifluoroethanol/anti-solvent mixtures.

TABLE 11

Observations from Anti-solvent Addition Cooling/Temperature Cycling Crystallizations

| Sample ID | Solvent | Anti-solvent | % Solvent | % Anti-solvent | Observation at 50° C., after addition of anti-solvent | Observation after temperature cycling (at 5° C.) | Observation before isolation |
|---|---|---|---|---|---|---|---|
| 1 | Methanol | Acetonitrile | 73.7 | 26.3 | Clear solution | Slurry | Slurry |
| 2 | Methanol | EA | 73.7 | 26.3 | Clear solution | Slurry | Slurry |
| 3 | Methanol | THF | 73.7 | 26.3 | Clear solution | Slurry | Slurry |
| 4 | Methanol | Acetone | 73.7 | 26.3 | Clear solution | Slurry | Slurry |
| 5 | Methanol | MEK | 73.7 | 26.3 | Clear solution | Slurry | Slurry |
| 6 | Methanol | Toluene | 73.7 | 26.3 | Clear solution | Thin Slurry | Thin Slurry |
| 7 | Methanol | Heptane | 73.7 | 26.3 | Clear solution | Slurry | Slurry |
| 8 | Ethanol | EA | 74.4 | 25.6 | Precipitation | Thick precipitation | Slurry |
| 9 | Ethanol | THF | 74.4 | 25.6 | Clear/slight turbid | Thick precipitation | Slurry |
| 10 | Ethanol | Acetone | 74.4 | 25.6 | Clear solution | Thick slurry | Thin slurry |
| 11 | Ethanol | MEK | 74.4 | 25.6 | Slight turbid | Thick precipitation | Slurry |
| 12 | Ethanol | Toluene | 74.4 | 25.6 | Clear solution | Thick precipitation | Slurry |
| 13 | Ethanol | Heptane | 74.4 | 25.6 | Turbid | Thick precipitation | Slurry |
| 14 | Ethanol | TBME | 74.4 | 25.6 | Thin slurry | Thick precipitation | Slurry |
| 15 | Ethanol | Acetonitrile | 74.4 | 25.6 | Clear solution | Slurry | Thin slurry |

TABLE 11-continued

Observations from Anti-solvent Addition Cooling/Temperature Cycling Crystallizations

| Sample ID | Solvent | Anti-solvent | % Solvent | % Anti-solvent | Observation at 50° C., after addition of anti-solvent | Observation after temperature cycling (at 5° C.) | Observation before isolation |
|---|---|---|---|---|---|---|---|
| 16 | Trifluoroethanol | EA | 50.0 | 50.0 | Thick precipitation | Thick precipitation | Slurry |
| 17 | Trifluoroethanol | THF | 50.0 | 50.0 | Thick precipitation | Thick precipitation | Slurry |
| 18 | Trifluoroethanol | Acetone | 50.0 | 50.0 | Thick precipitation | Thick precipitation | Slurry |
| 19 | Trifluoroethanol | MEK | 50.0 | 50.0 | Slurry | Thick precipitation | Slurry |
| 20 | Trifluoroethanol | Toluene | 50.0 | 50.0 | Clear solution | Clear solution | Clear solution |
| 21 | Trifluoroethanol | Heptane | 50.0 | 50.0 | Slight turbid | Slight tuibid | Slight Turbid |
| 22 | Trifluoroethanol | TBME | 50.0 | 50.0 | Thick slurry precipitation | Thick | Slurry |
| 23 | Trifluoroethanol | Acetonitrile | 50.0 | 50.0 | Thick precipitation | Thick precipitation | Slurry |

TABLE 12

Results from Anti-solvent Addition Cooling/Temperature Cycling Crystallizations

| Sample ID | Solvent/solvent system | Anti-solvent | % Solvent | % anti-solvent | XRPD analysis | Purity by HPLC (%) |
|---|---|---|---|---|---|---|
| 1 | Methanol | Acetonitrile | 73.4 | 26.6 | Crystalline | 97.86 |
| 2 | Methanol | EA | 73.7 | 26.3 | Crystalline | 98.19 |
| 3 | Methanol | THF | 73.7 | 26.3 | Crystalline | 96.43 |
| 4 | Methanol | Acetone | 73.7 | 26.3 | Crystalline | 97.86 |
| 5 | Methanol | MEK | 73.7 | 26.3 | Crystalline | 97.88 |
| 6 | Methanol | Toluene | 73.7 | 26.3 | Crystalline | 97.46 |
| 7 | Methanol | Heptane | 73.7 | 26.3 | Crystalline | 97.70 |
| 8 | Ethanol | EA | 74.4 | 25.6 | Poorly crystalline | 98.01 |
| 9 | Ethanol | THF | 74.4 | 25.6 | Poorly crystalline | 96.69 |
| 10 | Ethanol | Acetone | 74.4 | 25.6 | Partially crystalline | 98.59 |
| 11 | Ethanol | MEK | 74.4 | 25.6 | Partially crystalline | 98.31 |
| 12 | Ethanol | Toluene | 74.4 | 25.6 | Partially crystalline | 98.03 |
| 13 | Ethanol | Heptane | 74.4 | 25.6 | Partially crystalline | 98.11 |
| 14 | Ethanol | TBME | 74.4 | 25.6 | Partially crystalline | 97.87 |
| 15 | Ethanol | Acetonitrile | 74.4 | 25.6 | Partially crystalline | 98.66 |
| 16 | Trifluoro-ethanol | EA | 50.0 | 50.0 | Partially crystalline | 97.10 |
| 17 | Trifluoro-ethanol | THF | 50.0 | 50.0 | Partially crystallite | 97.41 |
| 18 | Trifluoro-ethanol | Acetone | 50.0 | 50.0 | Poorly crystalline | 97.31 |
| 19 | Trifluoro-ethanol | MEK | 50.0 | 50.0 | Poorly crystalline | 97.99 |
| 20 | Trifluoro-ethanol | Toluene | 50.0 | 50.0 | | |
| 21 | Trifluoro-ethanol | Heptane | 50.0 | 50.0 | | |
| 22 | Trifluoro-ethanol | TBME | 50.0 | 50.0 | Poorly crystalline | 97.71 |
| 23 | Trifluoro-ethanol | Acetonitrile | 50.0 | 50.0 | Poorly crystalline | 97.47 |

Anti-Solvent Addition Crystallizations

Further anti-solvent addition crystallizations were carried out using methanol and ethanol as the solvents with anti-solvents (75% v/v) added at 50° C. and 5° C. The anti-solvents used were acetonitrile, ethyl acetate, THF, acetone, MEK, toluene, TBME and heptane. The following results and observations were obtained from these experiments:

The wet material isolated from methanol/anti-solvent mixtures was free flowing but the wet material from ethanol/anti-solvents and trifluoroethanol/anti-solvents was gel like.

Observations and results are summarized in Table 13 and Table 14 respectively.

XRPD analysis on the isolated material revealed that crystalline material was produced from methanol/anti-solvent mixtures except from the methanol/toluene mixture at 50° C. where a partially crystalline material was observed. Predominantly amorphous to partially crystalline material was produced from ethanol/anti-solvent mixtures.

TABLE 13

Observations from Cooling/Temperature Cycling Crystallizations using Solvent/Anti-solvent Mixtures

| Sample ID | Solvent/solvent system | Anti-solvent | Temperature | % Solvent | % anti-solvent | Observation at 50° C. | Observation after Anti-solvent addition | Observations at 5° C. (after temperature cycling) |
|---|---|---|---|---|---|---|---|---|
| 1 | Methanol | Acetonitrile | 50° C. | 25 | 75 | Clear solution | Clear solution followed by slow crystallization | Thick slurry |
| 2 | | EA | | 25 | 75 | Clear solution | Clear solution followed by slow crystallization | Thick slurry |
| 3 | | THF | | 25 | 75 | Clear solution | Clear solution | Slurry (very slow crystallization) |
| 4 | | Acetone | | 25 | 75 | Clear solution | Clear solution followed by slow crystallization | Thick slurry |
| 5 | | MEK | | 25 | 75 | Clear solution | Clear solution followed by slow crystallization | Thick slurry |
| 6 | | Toluene | | 25 | 75 | Clear solution | Clear solution followed by slow crystallization | Thick slurry |
| 7 | | TBME | | 25 | 75 | Clear solution | Clear solution followed by slow crystallization | Thick slurry |
| 8 | Ethanol | Acetonitrile | 50° C. | 25 | 75 | Clear solution | Clear solution | Thick slurry (Gel like) |
| 9 | | EA | | 25 | 75 | Clear solution | Clear solution | Thick slurry (Gel like) |
| 10 | | THF | | 25 | 75 | Clear solution | Clear solution | Slurry (Gel like) |
| 11 | | Acetone | | 25 | 75 | Clear solution | Clear solution | Thick slurry (Gel like) |
| 12 | | MEK | | 25 | 75 | Clear solution | Clear solution | Pale yellow slurry (Gel like) |
| 13 | | Toluene | | 25 | 75 | Clear solution | Clear solution | Thick slurry (Gel like) |
| 14 | | TBME | | 25 | 75 | Clear solution | Precipitation-Gel like | Thick slurry (Gel like) |
| 15 | | Heptane | | 25 | 75 | Clear solution | Turbid | Thick slurry (Gel like) |
| 16 | Methanol | Acetonitrile | 5° C. | 25 | 75 | Slurry | Thick precipitation | Thick slurry |
| 17 | | EA | | 25 | 75 | Slurry | Thick slurry | Slurry |
| 18 | | THF | | 25 | 75 | Slurry | Thick precipitation | Slurry |
| 19 | | Acetone | | 25 | 75 | Slurry | Thick precipitation | Slurry |
| 20 | | MEK | | 25 | 75 | Slurry | Thick precipitation | Slurry |
| 21 | | Toluene | | 25 | 75 | Slurry | Thick slurry | Slurry |
| 22 | | TBME | | 25 | 75 | Slurry | Thick slurry | Slurry |
| 23 | Ethanol | Acetonitrile | 5° C. | 25 | 75 | Turbid | Thick precipitation | Slurry |
| 24 | | EA | | 25 | 75 | Slight Turbid | Thick precipitation | Slurry |
| 25 | | THF | | 25 | 75 | Slight Turbid | Thick precipitation | Thin slurry |
| 26 | | Acetone | | 25 | 75 | Slight Turbid | Thick precipitation | Thin slurry |
| 27 | | MEK | | 25 | 75 | Slight Turbid | Thick precipitation | Thin slurry |
| 28 | | Toluene | | 25 | 75 | Slight Turbid | Thick precipitation | Very thin slurry |
| 29 | | TBME | | 25 | 75 | Slight Turbid | Thick precipitation | Thin slurry |
| 30 | | Heptane | | 25 | 75 | Slight Turbid | Thick precipitation | Thin slurry |

TABLE 14

Results from Cooling/Temperature Cycling Crystallizations using Solvent/Anti-solvent Mixtures

| Sample ID | Solvent | Anti-solvent | Temperature | % Solvent | % anti-solvent | XRPD | HPLC % |
|---|---|---|---|---|---|---|---|
| 1 | Methanol | Acetonitrile | 50° C. | 25.0 | 75.0 | Crystalline | 96.94 |
| 2 | | EA | | 25.0 | 75.0 | Crystalline | 97.26 |
| 3 | | THF | | 25.0 | 75.0 | Crystalline | 98.85 |
| 4 | | Acetone | | 25.0 | 75.0 | Crystalline | 97.49 |
| 5 | | MEK | | 25.0 | 75.0 | Crystallite | 97.81 |
| 6 | | Toluene | | 25.0 | 75.0 | Partially crystalline | 98.01 |
| 7 | | TBME | | 25.0 | 75.0 | Crystalline | 97.35 |
| 8 | Ethanol | Acetonitrile | 50° C. | 25.0 | 75.0 | Crystalline | 98.32 |
| 9 | | EA | | 25.0 | 75.0 | Partially crystalline | 96.76 |
| 10 | | THF | | 25.0 | 75.0 | Poorly crystalline | 95.94 |
| 11 | | Acetone | | 25.0 | 75.0 | Partially Crystalline | 98.87 |
| 12 | | MEK | | 25.0 | 75.0 | Predominantly amorphous | 97.49 |
| 13 | | Toluene | | 25.0 | 75.0 | Predominantly amorphous | 97.08 |
| 14 | | TBME | | 25.0 | 75.0 | Partially crystalline | 98.81 |
| 15 | | Heptane | | 25.0 | 75.0 | Predominantly amorphous | 97.44 |
| 16 | Methanol | Acetonitrile | 5° C. | 25 | 75 | Crystalline | 97.6 |
| 17 | | EA | | 25 | 75 | Crystalline | 97.55 |
| 18 | | THF | | 25 | 75 | Crystalline | 97.57 |
| 19 | | Acetone | | 25 | 75 | Crystalline | 97.55 |
| 20 | | MEK | | 25 | 75 | Crystalline | 97.42 |
| 21 | | Toluene | | 25 | 75 | Crystalline | 97.30 |
| 22 | | TBME | | 25 | 75 | Crystalline | 97.12 |
| 23 | Ethanol | Acetonitrile | 5° C. | 25 | 75 | Partially crystalline | 98.95 |
| 24 | | EA | | 25 | 75 | Partially crystalline | 98.02 |
| 25 | | THF | | 25 | 75 | Partially crystalline | 97.85 |
| 26 | | Acetone | | 25 | 75 | Partially crystalline | 98.42 |
| 27 | | MEK | | 25 | 75 | Partially crystalline | 98.52 |
| 28 | | Toluene | | 25 | 75 | Predominantly amorphous | 97.42 |
| 29 | | TBME | | 25 | 75 | Partially crystalline | 98.51 |
| 30 | | Heptane | | 25 | 75 | Partially crystalline | 97.44 |

Seeded Cooling Crystallization using Solvent/Anti-Solvent Mixtures

Crystalline Boc-D-Arg-DMT-Lys(Boc)-Phe-NH$_2$ was previously obtained from methanol and methanol/anti-solvent mixtures by cooling/temperature cycling crystallizations. The same crystalline form was observed and was designated as Form 1. Seeded cooling crystallizations of Boc-D-Arg-DMT-Lys(Boc)-Phe-NH$_2$ using solvent/anti-solvent mixtures were carried out, where crystallizations were seeded using Form 1 at 50° C. followed by a slow cool to 5° C. The following results and observations were obtained from these experiments:

After seeding with Form 1 at 50° C., seed persisted and further nucleation was observed during granulation at 50° C. in every experiment.

At 5° C., a thick slurry was observed.

The material isolated from methanol/anti-solvent mixtures was free flowing. Ethanol/anti-solvents produced gel-like material and after drying this material was observed to be partially glass-like.

Observations and results are summarized in Table 15 and Table 16 respectively.

XRPD analysis on the isolated material revealed that crystalline material was produced from methanol/anti-solvent mixtures. Partially crystalline material was observed from ethanol/anti-solvent mixtures

TABLE 15

Observations from Seeded Cooling Crystallizations using Solvent/Anti-solvent Mixtures

| Sample ID | Solvent | Anti-solvent/ co-solvent | % Solvent | % anti-solvent/ co-solvent | Observations at 50° C. | Observations after Anti-solvent addition at 50° C. | Observations after granulation for 1 hour at 50° C. (after seeding) | Observations at 5° C. (cooling) | Observations before isolation |
|---|---|---|---|---|---|---|---|---|---|
| 1 | Methanol | Acetone | 75 | 25 | Clear solution | Clear solution | Thin slurry-crystallization | Thick slurry | Slurry |
| 2 | Methanol | 2-propanol | 75 | 25 | Clear solution | Clear solution | Thin slurry-crystallization | Thick slurry | Slurry |
| 3 | Methanol | 2-butanol | 75 | 25 | Clear solution | Clear solution | Thin slurry-crystallization | Thick precipitation | Slurry |
| 4 | Methanol | TBME | 75 | 25 | Clear solution | Clear solution | Thin slurry-crystallization | Thick precipitation | Slurry |
| 5 | Methanol | Ethanol | 50 | 50 | Clear solution | Clear solution | Thin slurry-crystallization | Thick slurry | Slurry |
| 6 | Ethanol | 2-propanol | 75 | 25 | Clear solution | Clear solution | Thin slurry-crystallization | Thick precipitation | Slurry |
| 7 | Ethanol | 2-butanol | 75 | 25 | Clear solution | Clear solution | Thin slurry-crystallization | Thick precipitation | Slurry |

TABLE 16

Results from Seeded Cooling Crystallizations using Solvent/Anti-solvent Mixtures

| Sample ID | Solvent | Anti-solvent/co-solvent | % Solvent | % anti-solvent/co-solvent | Observations before Isolation | XPRD | HPLC (%) |
|---|---|---|---|---|---|---|---|
| 1 | Methanol | Acetone | 75 | 25 | Slurry | Crystalline | 97.81 |
| 2 | Methanol | 2-propanol | 75 | 25 | Slurry | Crystalline | 97.95 |
| 3 | Methanol | 2-butanol | 75 | 25 | Slurry | Crystalline | 98.27 |
| 4 | Methanol | TBME | 75 | 25 | Slurry | Crystalline | 98.27 |
| 5 | Methanol | Ethanol | 50 | 50 | Slurry | Crystalline | 97.69 |
| 6 | Ethanol | 2-propanol | 75 | 25 | Slurry | Partially crystalline | 97.72 |
| 7 | Ethanol | 2-butanol | 75 | 25 | Slurry | Partially crystalline | 97.58 |

Scale-Up Seeded Cooling Crystallizations Using Solvent/Anti-Solvent Mixtures

Crystallization scale-up experiments were carried out with Boc-D-Arg-DMT-Lys(Boc)-Phe-NH$_2$ on a ca. 250 mg scale, using methanol, methanol/acetonitrile, methanol/THF and ethanol/acetone solvent systems. The following results and observations were obtained from these experiments:

After seeding at 50° C., seed persisted and further nucleation was observed during granulation at 50° C. for every experiment.

At 5° C., either a thick slurry or freely stirrable slurry was observed.

The material isolated from methanol and methanol/anti-solvent mixtures was free flowing, the ethanol/acetone solvent system produced a gel-like material and after drying the material was observed to be partially glass-like.

Observations and results are summarized in Table 17 and Table 18 respectively. Methanol (100 mg/mL)

XRPD analysis on the isolated material showed that crystalline material was produced.

PLM analysis of the dried material indicated that the material was birefringent with no well-defined morphology.

TG/DTA showed a weight loss of ca. 1.97% from the outset up to ca. 169° C. An endothermic event was observed at an onset of 169.2° C. (peak at 178.7° C.) in the DTA.

The experiment produced crystalline material with a 85.06% theoretical yield.

HPLC analysis on the dried material showed an uplift in purity from 97.5% (purity of input material) to 98.5%.

Methanol: Acetonitrile (75:25% v/v)

XRPD analysis on the isolated material showed that crystalline material was produced.

PLM analysis of the dried material indicated that the material was birefringent with no well defined morphology.

TG/DTA showed a weight loss of ca. 2.0% from the outset up to ca. 170° C. An endothermic event was observed at an onset of ca. 170.9° C. (peak at 180° C.) in the DTA.

The experiment produced crystalline material with a 88.97% theoretical yield.

HPLC analysis on the dried material showed an uplift in purity from 97.5% (purity of input material) to 98.6%.

Methanol:THF (25:75% v/v)

XRPD analysis on the isolated material showed that crystalline material was produced.

PLM analysis of the dried material indicated that the material was birefringent with no well-defined morphology.

TG/DTA showed a weight loss of ca. 1.79% from the outset up to ca. 165° C. An endothermic event was observed at an onset of 165.2° C. (peak at 173.1° C.) in the DTA.

The experiment produced crystalline material with a 31.57% theoretical yield.

HPLC analysis on the dried material showed an uplift in purity from 97.5% (purity of input material) to 99.2%.

Ethanol: Acetone (25:75% v/v)

XRPD analysis on the isolated material showed that predominantly amorphous material was produced.

PLM analysis of the dried material indicated that the material was non-birefringent.

TG/DTA showed a weight loss of ca. 1.3% from the outset up to ca. 144° C. An endothermic event was observed at an onset of 144.6° C. (peak at 153.4° C.) in the DTA. TG/DTA was observed to be similar to input Boc-D-Arg-DMT-Lys(Boc)-Phe-NH$_2$, predominantly amorphous material.

The experiment produced predominantly amorphous material with a 84.39% theoretical yield.

HPLC analysis on the dried material showed an uplift in purity from 97.5% (purity of input material) to 98.4%.

fumaric acid, benzoic acid and succinic acid using acetone, acetonitrile:water (50:50% v/v), ethanol and methanol as solvent systems. The following results and observations were obtained from these experiments:

Salt Formation Using Hydrochloric Acid

After temperature cycling, gel-like material was observed when using acetone, acetonitrile:water (50:50% v/v) and ethanol. A slurry was observed when using methanol as the solvent.

XRPD analysis on the isolated material showed that crystalline material (Form 1, free base) was produced from methanol and predominantly amorphous material was produced from the acetone, acetonitrile: water (50:50% v/v) and ethanol solvent systems.

Salt Formation Using p-Toluene Sulfonic Acid

After temperature cycling, a clear solution with some solids at the bottom of the vial was observed using acetone as the solvent. Gel-like material was observed using acetonitrile:water (50:50% v/v), a slurry was observed using methanol and a clear solution was produced using ethanol.

XRPD analysis on the isolated material showed that partially crystalline material having an XRPD pattern different from the free base Form 1 was produced from acetone and acetonitrile: water (50:50% v/v). Partially

TABLE 17

Observations from Scale-up Seeded Cooling Crystallizations

| Sample ID | Solvent | Anti-solvent | Solvent | Anti-solvent | Observation at 50° C. before addition of anti-solvent | Observations after addition of anti solvent at 50° C. | Observations after granulation for 1 hour at 50° C. (after seeding) | Observations at 5° C. |
|---|---|---|---|---|---|---|---|---|
| 1 | Methanol | | 100.00 | | Clear solution | N/A | Thin slurry-crystallization | Thick Slurry |
| 2 | Methanol | Acetonitrile | 75.00 | 25.00 | Clear solution | Clear solution | Thin slurry-crystallization | Thick Slurry |
| 3 | Methanol | THF | 25.00 | 75.00 | Clear solution | Clear solution | Thin slurry-crystallization | Slurry |
| 4 | Ethanol | Acetone | 25.00 | 75.00 | Clear solution | Clear solution | Thin slurry-crystallization | Slurry (Gel-like material) |

TABLE 18

Results from Scale-up Seeded Cooling Crystallizations

| Sample ID | Solvent | Anti-solvent | XRPD | Solid Purity % Area | Mean Purity % Area (Mother Liquor) | Mean Conc. In Mother Liquor mg/mL | Theoretical yield (%) |
|---|---|---|---|---|---|---|---|
| 1 | Methanol | | Crystalline | 98.51 | 97.69 | 94.94 | 85.06 |
| 2 | Methanol | Acetonitrile | Crystalline | 98.63 | 97.66 | 91.93 | 88.97 |
| 3 | Methanol | THF | Crystalline | 99.24 | 98.98 | 38.97 | 31.57 |
| 4 | Ethanol | Acetone | Predominantly amorphous | 98.44 | 96.48 | 10.38 | 84.39 |

Primary Salt Screening

A limited salt screen was carried out on Boc-D-Arg-DMT-Lys(Boc)-Phe-NH$_2$ with the aim of locating crystalline salts in order to assess the potential for purification through salt formation.

Salt screening on Boc-D-Arg-DMT-Lys(Boc)-Phe-NH$_2$ was carried out using hydrochloric acid, p-toluenesulfonic acid, methane sulfonic acid, oxalic acid, L-tartaric acid, crystalline material, having some peaks in common with the free base Form 1 was observed from methanol.

Salt Formation Using Methane Sulfonic Acid

After temperature cycling, a slurry was observed using acetone and ethanol, gel-like material was observed using acetonitrile: water (50:50% v/v) and a clear solution was produced from methanol as the solvent.

XRPD analysis on the isolated material showed that partially crystalline material having an XRPD pattern different from free base Form 1 was produced from acetone and acetonitrile:water (50:50% v/v). Predominantly amorphous material was observed from ethanol.

Salt Formation Using Oxalic Acid

After temperature cycling, a gel-like material was observed using acetonitrile: water (50:50% v/v) and ethanol. A slurry was observed when using acetone and methanol as the solvents.

XRPD analysis on the isolated material revealed that crystalline material (Free base, Form 1) was produced from methanol, predominantly amorphous material was produced from ethanol and a partially crystalline material having an XRPD pattern different from free base Form 1 was produced from acetonitrile: water (50:50% v/v). Crystalline material having an XRPD pattern different from free base Form 1 was observed from acetone.

Salt Formation Using L-Tartaric Acid

After temperature cycling, a slurry was observed when using acetone and methanol, whilst a gel-like material was observed when using acetonitrile: water (50:50% v/v) and ethanol.

XRPD analysis on the isolated material revealed that crystalline material (Free base, Form 1) was produced from methanol and predominantly amorphous material was produced form acetone and ethanol. Partially crystalline material having an XRPD pattern different from free base Form 1 was produced from acetonitrile: water (50:50% v/v).

Salt Formation Using Fumaric Acid

After temperature cycling, a slurry was observed when using acetone and methanol, whilst a gel-like material was observed when using acetonitrile: water (50:50% v/v) and ethanol.

XRPD analysis on the isolated material showed that crystalline material (Free base, Form 1) was produced from methanol and predominantly amorphous material was produced form acetone and ethanol. Partially crystalline material having an XRPD pattern different from the free base Form 1 was produced from acetonitrile: water (50:50% v/v).

Salt Formation Using Benzoic Acid

After temperature cycling, gel-like material was observed using acetonitrile: water (50:50% v/v) and ethanol. A slurry was observed when using acetone as the solvent. Solid was observed from methanol.

XRPD analysis on the isolated material revealed that poorly crystalline material (Free base, Form 1) was produced from acetone and ethanol. Crystalline material (slightly different from free base Form 1) was produced from acetonitrile: water (50:50% v/v) and methanol.

Salt Formation Using Succinic Acid

After temperature cycling, a gel-like material was observed when using acetonitrile: water (50:50% v/v) and a slurry was observed when using ethanol or methanol as the solvent.

Solid was observed from acetone.

XRPD analysis on the isolated material showed that partially crystalline material (Free base, Form 1) was produced from acetone, ethanol and methanol. Poorly crystalline material (slightly different from free base Form 1) was produced from acetonitrile: water (50:50% v/v).

Observations are summarized in Table 19 and Table 20 and results are summarized in Table 21 and Table 22.

TABLE 19

Observations from Primary Salt Screening

| Sample ID | Solvent/ solvent system | Counterion | Initial observations at 50° C. | Observation before addition of counterion solution/slurry at 50° C. | Observation after addition of counterion solution at 50° C. | Observation after temperature cycle (16 hours) | Observation after temperature cycling (40 hours) |
|---|---|---|---|---|---|---|---|
| 1 | Acetone | HCl | Slurry | Slurry | Slurry | Gel like | Gel like |
| 2 | Acetonitrile: water (50:50% v/v) | | Clear solution followed by precipitation: slurry | Clear solution | Slurry | Gel like | Gel like |
| 3 | Ethanol | | Clear solution followed by precipitation: slurry | Turbid | Clear solution | Gel like | Gel like |
| 4 | Methanol | | Clear solution followed by precipitation: slurry | Slurry | Slurry | Slurry | Slurry |
| 5 | Acetone | P-toluene sulfonic acid | Slurry | Slurry | Clear solution | Clear solution/ some solids at the bottom | Clear solution/ some solids at the bottom |
| 6 | Acetonitrile: water (50:50% v/v) | | Clear solution followed by precipitation: slurry | Clear solution | Turbid | Gel like | Gel like |

TABLE 19-continued

Observations from Primary Salt Screening

| Sample ID | Solvent/ solvent system | Counterion | Initial observations at 50° C. | Observation before addition of counterion solution/slurry at 50° C. | Observation after addition of counterion solution at 50° C. | Observation after temperature cycle (16 hours) | Observation after temperature cycling (40 hours) |
|---|---|---|---|---|---|---|---|
| 7 | Ethanol | | Clear solution followed by precipitation: slurry | Slurry | Clear solution | Clear solution | Clear solution |
| 8 | Methanol | | Clear solution followed by precipitation: slurry | Slurry | Slurry | Slurry | Slurry |
| 9 | Acetone | Methane sulfonic acid | Slurry | Slurry | Slurry | Slurry | Slurry |
| 10 | Acetonitrile: water (50:50% v/v) | | Clear solution followed by precipitation: slurry | Slurry | Clear solution | Gel like | Gel like |
| 11 | Ethanol | | Clear solution followed by precipitation: slurry | Turbid | Slight Turbid | Slurry | Slurry |
| 12 | Methanol | | Clear solution followed by precipitation: slurry | Slurry | Clear solution | Clear solution | Clear solution |
| 13 | Acetone | Oxalic Acid | Slurry | Slurry | Slurry | Slurry | Slurry |
| 14 | Acetonitrile: water (50:50% v/v) | | Clear solution followed by precipitation: slurry | Clear solution | Clear solution | Gel like | Gel like |
| 15 | Ethanol | | Clear solution followed by precipitation: slurry | Turbid | Slurry | Gel like | Gel like |
| 16 | Methanol | | Clear solution followed by precipitation: slurry | Slurry | Slurry | Slurry | Slurry |

TABLE 20

Observations from Primary Salt Screening

| Sample ID | Solvent/ solvent system | Counterion | Initial observations at 50° C. | Observation before addition of counterion solution/ slurry at 50° C. | Observation after addition of counterion solution at 50° C. | Observation after temperature cycle (16 hours) | Observation after temperature cycling (40 hours) |
|---|---|---|---|---|---|---|---|
| 17 | Acetone | L-Tartaric Acid | Slurry | Slurry | Slurry | Slurry | Slurry |
| 18 | Acetonitrile: water (50:50% v/v) | | Clear solution followed by precipitation: slurry | Slurry | Slurry | Gel like | Gel like |
| 19 | Ethanol | | Clear solution followed by precipitation: slurry | Slurry | Slurry | Gel like | Gel like |

TABLE 20-continued

Observations from Primary Salt Screening

| Sample ID | Solvent/ solvent system | Counterion | Initial observations at 50° C. | Observation before addition of counterion solution/ slurry at 50° C. | Observation after addition of counterion solution at 50° C. | Observation after temperature cycle (16 hours) | Observation after temperature cycling (40 hours) |
|---|---|---|---|---|---|---|---|
| 20 | Methanol | | Clear solution followed by precipitation: slurry | Slurry | Slurry | Slurry | Slurry |
| 21 | Acetone | Fumaric Acid | Slurry | Slurry | Slurry | Slurry | Slurry |
| 22 | Acetonitrile: water (50:50% v/v) | Acid | Clear solution followed by precipitation: slurry | Clear solution | Clear solution | Gel like | Gel like |
| 23 | Ethanol | | Clear solution followed by precipitation: slurry | Turbid | Clear solution | Gel like | Gel like |
| 24 | Methanol | | Clear solution followed by precipitation: slurry | Slurry | Slurry | Slurry | Slurry |
| 25 | Acetone | Benzoic Acid | Slurry | Slurry | Slurry | Slurry | Slurry |
| 26 | Acetonitrile: water (50:50% v/v) | | Clear solution followed by precipitation: slurry | Clear solution | Clear solution | Gel like | Gel like |
| 27 | Ethanol | | Clear solution followed by precipitation: slurry | Turbid | Clear solution | Gel like | Gel like |
| 28 | Methanol | | Clear solution followed by precipitation: slurry | Slurry | Slurry | Solid | Dry solid |
| 29 | Acetone | Succinic Acid | Slurry | Slurry | Slurry | Solid | Dry solid |
| 30 | Acetonitrile: water (50:50% v/v) | | Clear solution followed by precipitation: slurry | Turbid | Clear solution | Gel like | Gel like |
| 31 | Ethanol | | Clear solution followed by precipitation: slurry | Turbid | Slurry | Slurry | Slurry |
| 32 | Methanol | | Clear solution followed by precipitation: slurry | Slurry | Slurry | Slurry | Slurry |

TABLE 21

Results from Primary Salt Screening

| Sample ID | Solvent/Solvent system | Counter-ion | XRPD | % Purity by HPLC |
|---|---|---|---|---|
| 1 | Acetone | HCl | Predominantly Amorphous (Same as input material) | |
| 2 | Acetonitrile:water (50:50% v/v) | | Poorly Crystalline (slightly different than input material) | 97.94 |
| 3 | Ethanol | | Predominantly Amorphous (Same as input material) | |
| 4 | Methanol | | Crystalline, same form as crystalline free material | |
| 5 | Acetone | P-toluene sulfonic acid | Partially crystalline (different form from crystalline free material) | 99.25 |
| 6 | Acetonitrile:water (50:50% v/v) | | Poorly Crystalline (slightly different than input material) | 89.97 |
| 7 | Ethanol | | | |
| 8 | Methanol | | Partially crystalline (some peaks matching with the crystalline free material) | |
| 9 | Acetone | Methane sulfonic acid | Partially crystalline (different form from crystalline free material) | 84.44 |
| 10 | Acetonitrile:water (50:50% v/v) | | Poorly Crystalline (slightly different than input material) | |
| 11 | Ethanol | | Predominantly Amorphous (slightly different than input material) | |
| 12 | Methanol | | | |
| 13 | Acetone | Oxalic Acid | Crystalline (different form from crystalline free material) | 98.02 |
| 14 | Acetonitrile:water (50:50% v/v) | | Poorly Crystalline (slightly different than input material) | 87.29 |
| 15 | Ethanol | | Predominantly Amorphous (Same as input material) | |
| 16 | Methanol | | Crystalline, same form as crystalline free material | |

TABLE 22

Results from Primary Salt Screening

| Sample ID | Solvent/Solvent system | Counterion | XRPD | % Purity by HPLC |
|---|---|---|---|---|
| 17 | Acetone | L-Tartaric acid | Predominantly amorphous (slightly different than input material) | |
| 18 | Acetonitrile:water (50:50% v/v) | | Poorly crystalline (slightly different than input material) | 98.64 |
| 19 | Ethanol | | Poorly crystalline (slightly different than input material) | |
| 20 | Methanol | | Crystalline, same form as crystalline free material | |
| 21 | Acetone | Fumaric acid | Predominantly amorphous (same as input material) | |
| 22 | Acetonitrile:water (50:50% v/v) | | Poorly crystalline (slightly different than input material) | 98.65 |
| 23 | Ethanol | | Predominantly amorphous (mixture of input free material and crystalline free material) | |
| 24 | Methanol | | Crystalline, same form as crystalline free material | |
| 25 | Acetone | Benzoic acid | Poorly crystalline (similar to crystalline free material) | |
| 26 | Acetonitrile:water (50:50% v/v) | | Crystalline (slightly different from crystalline free material) | 98.71 |
| 27 | Ethanol | | Poorly crystalline, similar form as crystalline free material) | |
| 28 | Methanol | | Crystalline (slightly different than crystalline free material) | 98.97 |
| 29 | Acetone | Succinic acid | Partially crystalline (mixture of input free material and crystalline free material) | |
| 30 | Acetonitrile:water (50:50% v/v) | | Poorly crystalline (slightly different than input material) | 98.68 |
| 31 | Ethanol | | Partially crystalline, same form as crystalline free material | |
| 32 | Methanol | | Partially crystalline, same form as crystalline free material | |

Summary of Results

Initial characterization of Boc-D-Arg-DMT-Lys (Boc)-Phe-NH$_2$, showed it to be predominantly amorphous by XRPD analysis and non-birefringent by PLManalysis, exhibiting no clearly defined morphology. TG/DT analysis showed a weight loss of ca. 2.79% from the outset up to ca. 144° C., followed by a weight loss of ca. 0.72%, associated with an endothermic event at ca. 144.3° C. (onset ca. 155.2° C.). DSC analysis showed a broad endothermic event from the outset up to ca. 140° C. with a further endothermic event observed at ca. 155.6° C. (onset at ca. 140.2° C.). KF analysis indicated a water content of ca. 3.61%, while GVS analysis indicated the material was highly hygroscopic, with a mass increase of ca. 10% from 40-90% RH. The purity of the received material was 97.50% by HPLC.

An approximate solvent solubility screen was carried out using 19 solvent systems and yielded a range of solubilities. The received material was found to be highly soluble, with methanol, trifluoroethanol, acetonitrile:water (50:50% v/v) and DMSO:acetone (50:50% v/v) giving solubility values of ≥200 mg/mL. A solubility of ca. 140 mg/mL was obtained in ethanol with a ca. 100 mg/mL solubility observed in 2-propanol:water (50:50% v/v) and ethanol:water (50:50% v/v). Moderate solubility (ca. 58 to 24 mg/mL) was observed in acetone:water (50:50 v/v), methanol:water (50:50 v/v), and DMSO:water (50:50 v/v), with poor solubility (<17 mg/mL) obtained in all other solvent systems investigated, including acetone, dichloromethane, 2-butanol, 2-propanol, methyl ethyl ketone, toluene, THF, ethyl acetate and acetonitrile. The residual solids from some of the solvent systems showing poor solubility were analyzed by XRPD after slurrying at 50° C. overnight, but all diffractograms indicated that the material remained predominantly amorphous.

Small-scale crystallization screening experiments were carried out investigating cooling, temperature cycling, anti-solvent addition and seeding techniques. Cooling followed by temperature cycling crystallizations were carried out using seven different initial solvent mixtures. The material was dissolved in ethanol, methanol, trifluoroethanol, acetone:water (50:50% v/v, Acetonitrile:water (50:50% v/v) and DMSO:water (80:20% v/v) at 50° C. The solutions were cooled down to 5° C. then temperature cycled between 40° C. and 5° C. Crystallization of material at 50° C. was observed with methanol at both the process concentrations of 150 mg/mL and 100 mg/mL and crystalline material was isolated (Form 1) which was birefringent by PLM analysis, with no defined morphology. The purity of the solid isolated from methanol was 98.24% (ca. 150 mg/mL) and 98.62% (ca. 100 mg/mL), indicating that crystallization offered purity uplift over the input predominantly amorphous material. Predominantly amorphous solids were isolated from ethanol and acetone: water (50:50% v/v) showing purity values of 98.80% and 98.81%, indicating a purity uplift over the input material, however the wet material isolated from these solvent systems was gel-like. The other solvent systems did not yield solids.

Anti-solvent addition followed by cooling/temperature cycling crystallizations were carried out using 23 solvent/anti-solvent mixtures. The material was dissolved in ethanol, methanol, and trifluoroethanol at 50° C. Anti-solvents acetonitrile, ethyl acetate, THF, acetone, MEK, toluene, heptane and TBME (for ethanol and trifluoroethanol) were added at 50° C. to achieve ratios of methanol/anti-solvent (73.7:26.3% v/v), ethanol/anti-solvent (74.4:25.6% v/v) and trifluoroethanol/anti-solvent (50:50% v/v). Clear solutions were observed at 50° C. with methanol/anti-solvents but for ethanol/anti-solvent mixtures and trifluoroethanol/anti-solvent mixtures for most experiments turbidity to thick precipitation was observed. The crystallizations were cooled down to 5° C. then temperature cycled between 40° C. and 5° C. Crystalline material was isolated from methanol/antisolvent mixtures (Form 1). The purity values of the solids isolated from methanol/anti-solvent mixtures were between 96.43% and 98.19%, indicating that the crystallization offered a purity uplift for some of the methanol/anti-solvent mixtures. Poorly crystalline to partially crystalline solids were isolated from ethanol/anti-solvent mixtures and trifluoroethanol/anti-solvent mixtures. Purity of the solids was between 96.69% and 98.66%, but the wet material isolated from these solvent systems was gel-like.

Further anti-solvent addition crystallizations were carried out using 15 solvent/anti-solvent mixtures. The material was dissolved in methanol and ethanol at 50° C. Anti-solvents acetonitrile, ethyl acetate, THF, acetone, MEK, toluene, TBME and heptane (for ethanol) were added at 50° C. and 5° C. to achieve solvent/anti-solvent ratios of (25:75% v/v). Crystalline material was isolated from methanol/anti-solvent mixtures except from the methanol/toluene mixture at 50° C., where partially crystalline material was observed. The maximum uplift of purity was observed from methanol/THF (THF addition at 50° C.) where a purity of 98.85% was afforded. Predominantly amorphous to partially crystalline material was produced from ethanol/anti-solvent mixtures with a maximum uplift of purity (98.95%) observed from ethanol/acetonitrile (acetonitrile addition at 5° C.). The wet material isolated from ethanol/anti-solvent mixtures was however gel-like.

Seeded anti-solvent addition crystallizations using solvent/anti-solvent mixtures were carried out in 7 solvent systems. For methanol/anti-solvent mixtures (75:25% v/v), acetone, 2-propanol, 2-butanol, TBME were used as the anti-solvents and a methanol/ethanol (50:50% v/v) ratio was also used. For ethanol/anti-solvent mixtures (75:25% v/v), 2 propanol and 2-butanol were used as the anti-solvents. The material was dissolved in methanol and ethanol at 50° C. Anti-solvents were added at 50° C., affording clear solutions. The clear solutions were seeded with Form 1 at 50° C. followed by granulation for 1 hour where crystallization was observed. The crystallizations were cooled down to 5° C. Crystalline material was isolated from methanol/anti-solvent mixtures and partially crystalline material from ethanol/anti-solvent mixtures. The maximum uplift in purity was observed using methanol/2-butanol and methanol/TBME, showing a purity of 98.27% for both solvent systems.

The seeded anti-solvent addition cooling crystallizations were further scaled up to 250 mg scale using methanol (100 mg/mL), methanol/acetonitrile (75:25% v/v), methanol/THF (25:75% v/v) and ethanol/acetone (25:75% v/v) solvent systems. Crystalline material was isolated from methanol and methanol/anti-solvent mixtures and predominantly amorphous material from the ethanol/acetone system. The best result was obtained from methanol/acetonitrile with a theoretical yield of 88.97% and a purity of 98.63%. A purity of 99.24% was obtained from methanol/THF (25:75% v/v), but the theoretical yield was only 31%. The predominantly amorphous material obtained from ethanol/acetone (25:75% v/v) showed a purity of 98.44% with a theoretical yield of 84.39%.

A limited salt screen was carried out on Boc-D-Arg-DMT-Lys(Boc)-Phe-NH$_2$ with the aim of locating a crystalline salt and assessing potential purification through salt formation. The counter ions and solvent systems used for the salt screening included hydrochloric acid, p-toluenesulfonic acid, methane sulfonic acid, oxalic acid, L-tartaric acid fumaric acid, benzoic acid and succinic acid in acetone, acetonitrile:water (50:50% v/v), ethanol and methanol. The material was slurried/dissolved in the solvent systems at 50° C. In acetone, slurries were observed but in the remaining systems, clear solutions were obtained. Within 1 hour of granulation at 50° C., crystallization of material was observed and a slurry was present for every experiment. The experiments were further diluted with the respective solvent system to dissolve the crystallized material or to afford a stirrable slurry. The counterion solutions were added to the respective experiments at 50° C. The experiments were stirred at 50° C. and cooled down to 5° C. and then temperature cycled between 5° C. to 40° C. for ca. 40 hours.

Salt screening using Hydrochloric acid produced predominantly amorphous to poorly crystalline gel-like material, having a diffractogram slightly different from the input material in acetone, acetonitrile: water (50:50% v/v) and ethanol. Crystalline material (Form1, free base) was observed using methanol as the solvent.

Salt screening using p-Toluene sulfonic acid produced partially crystalline material having an XRPD pattern different from the free base Form 1 in acetone. $^1$H NMR analysis on the solids revealed salt formation and a purity of 99.25% was observed. Poorly crystalline gel-like material having a diffractogram slightly different from the input material was observed from acetonitrile:water (50:50% v/v) with a purity of 89.97%. Methanol produced partially crystalline material similar to the crystalline free base.

Salt screening using Methane sulfonic acid produced partially crystalline material having an XRPD pattern different from the free base Form 1 in acetone with a purity of 84.44%. Poorly crystalline and predominantly amorphous gel-like material having a diffractogram slightly different from the input material was observed from acetonitrile: water (50:50% v/v) and ethanol respectively.

Salt screening using Oxalic acid produced crystalline material having a XRPD pattern different from the crystalline free base Form 1 in acetone, with a purity of 98.02%. $^1$H NMR analysis on the solids indicated salt formation. Poorly crystalline gel-like material having a diffractogram slightly different from the input material was observed from acetonitrile: water (50:50% v/v) with a purity of 87.29%. No salt formation was observed using ethanol and methanol as solvents as these systems produced material having diffractograms identical to the input material and crystalline free base respectively.

Salt screening using L-Tartaric acid produced predominantly amorphous and poorly crystalline material having an XRPD pattern slightly different from the input material in acetone, acetonitrile:water (50:50% v/v) and ethanol respectively. Poorly crystalline material produced from acetonitrile:water (50:50% v/v) showed a purity of 98.64%. Crystalline free base Form 1 was produced from methanol.

Salt screening using Fumaric acid produced predominantly amorphous material having an XRPD pattern similar to the amorphous input and a pattern showing a mixture of crystalline and amorphous free base from acetone and ethanol respectively. Poorly crystalline material produced from acetonitrile: water (50:50% v/v) showed a purity of 98.65%. Crystalline free base Form 1 was produced from methanol.

Salt screening using Benzoic acid produced poorly crystalline material having an XRPD pattern similar to crystalline free base Form 1 from acetone and ethanol. Crystalline material having an XRPD pattern slightly different from crystalline free base Form 1 was produced from acetonitrile: water (50:50% v/v) and methanol with purities of 98.71% and 98.87% respectively.

Salt screening using Succinic acid produced partially crystalline material similar to crystalline form 1 was observed from acetone, ethanol and methanol. Poorly crystalline material produced from acetonitrile: water (50:50% v/v) showed a purity of 98.68%.

Overall, the crystallization screening study on Boc-D-Arg-DMT-Lys (Boc)-Phe-NH$_2$ indicated that crystalline material could be obtained by re-crystallization of the predominantly amorphous solid in methanol and methanol/anti-solvent mixtures. An uplift in purity was observed through crystallization of the intermediate. The primary salt screening study on Boc-D-Arg-DMT-Lys (Boc)-Phe-NH$_2$ resulted in crystalline material from oxalic acid in acetone having a different XRPD pattern compared with free base Form 1. Partially crystalline material having an XRPD pattern different from the free base Form 1 was obtained from p-toluene sulfonic acid in acetone. Further work would be required in order to better ascertain the nature of these solid forms Overall, crystalline material could be obtained by re-crystallization of the predominantly amorphous solid in methanol and in methanol/anti-solvent mixtures. The crystalline material was successfully produced at a 250 mg scale using methanol (100 mg/mL), methanol/acetonitrile (75:25% v/v) and methanol/THF (25:75% v/v). Using methanol/acetonitrile (75:25% v/v) we obtained a yield of 88.97% and purity of 98.63%. Limited salt screening resulted in crystalline and partially crystalline material when using oxalic acid and p-Toluenesulfonic acid in acetone, respectively. Both of the materials showed XRPD diffractgrams different from the crystalline free base Form 1. These salt formations also offered purity uplifts over the input material with a purity of 98.02% from the oxalic acid experiment and 99.25% from the p-Toluenesulfonic acid experiment.

The approximate solvent solubility screen utilized nineteen solvent systems and yielded a range of solubilities. The received material was found to be highly soluble, with methanol, trifluoroethanol, acetonitrile:water (50:50% v/v) and DMSO:acetone (50:50% v/v) giving solubility values of ≥200 mg/mL. A solubility of ca. 140 mg/mL was obtained in ethanol with a ca. 100 mg/mL solubility observed in 2-propanol:water (50:50% v/v) and ethanol:water (50:50% v/v). Moderate solubility (ca. 58 to 24 mg/mL) was obtained in acetone:water (50:50 v/v), methanol:water (50:50 v/v) and DMSO:water (50:50 v/v), with poor solubility (≤17 mg/mL) obtained in all other solvent systems investigated. The screen identified acetone, dichloromethane, 2-butanol, 2-propanol, methyl ethyl ketone, toluene, THF, ethyl acetate and acetonitrile as potential anti-solvents.

Small-scale crystallization screening experiments were carried out investigating cooling, temperature cycling, anti-solvent addition and seeding techniques. Cooling/temperature cycling crystallizations using methanol (at process concentrations of 150 mg/mL and 100 mg/mL) yielded crystalline material which were birefringent by PLM analysis, with no defined morphology. The purity of the crystallized solids isolated from methanol was 98.24% (ca. 150 mg/mL) and 98.62% (ca. 100 mg/mL), indicating that crystallization offered a purity uplift over the input predominantly amorphous material (97.5%). Crystallized wet material from acetone:water (50:50% v/v) and ethanol was gel-like and after drying, glass-like material was observed. Using water as part of the crystallization solvent was observed to be unsuitable for production of crystalline material, but ethanol was further investigated. Anti-solvent addition/cooling/temperature cycling crystallizations using methanol/anti-solvents (73:27% v.v) also produced crystalline material (Form 1). Ethanol/anti-solvents (74:46% v/v) and trifluoroethanol/anti-solvents (50:50% v/v) produced gel-like material which was observed to be poorly crystalline to partially crystalline, but an uplift in purity over the input material was observed with some of these solvent systems. Anti-solvent addition crystallizations, where anti-solvents (75% v/v) were added at 50° C. and 5° C. produced crystalline material using methanol/anti-solvent mixtures at both temperatures. Ethanol/anti-solvent (25:75% v/v) mixtures again produced gel-like material which dried to a glass-like solid. Seeded cooling crystallizations resulted in crystalline material from methanol/anti-solvent mixtures and partially crystalline material from ethanol/anti-solvent mixtures. When ethanol was used along with methanol (50:50% v/v), crystalline material was observed, however the use of ethanol along with other solvents did not allow for crystallization. An uplift in purity over the input material was observed with a maximum uplift of purity using methanol/2-butanol and methanol/TBME, where both experiments showed purities of 98.27%.

The seeded anti-solvent addition cooling crystallizations were further scaled up to 250 mg scale using methanol (100 mg/mL), methanol/Acetonitrile (75:25% v/v), methanol/THF (25:75% v/v) and ethanol/acetone (25:75% v/v). Crystalline material was isolated from methanol and methanol/anti-solvent mixtures and predominantly amorphous material from ethanol/acetone system. Using methanol/acetonitrile we obtained a yield of 88.97% and purity of 98.63%. A purity of 99.24% was obtained from methanol/THF (25:75% v/v), but the yield was only 31%. The predominantly amorphous material obtained from ethanol/acetone (25:75% v/v) showed a purity of 98.44% with a yield of 84.39%.

Limited salt screening was carried out on Boc-D-Arg-DMT-Lys(Boc)-Phe-NH$_2$, with the aim of locating a crystalline salt and assessing potential purification through salt formation. The screen entailed the use of hydrochloric acid, p-toluenesulfonic acid, methane sulfonic acid, oxalic acid, L-tartaric acid, fumaric acid, benzoic acid and succinic acid as the counterions in acetone, acetonitrile:water (50:50% v/v), ethanol and methanol solvent systems. Limited success was seen from the salt screen with crystalline material produced from oxalic acid in acetone and partially crystalline material from p-Toluene sulfonic acid in acetone, both having different XRPD patterns compared with the crystalline free base Form 1. All other salt formation reactions resulted in predominantly amorphous, poorly crystalline, partially crystalline and crystalline material having XRPD patterns similar to or only slightly different from the amorphous received material or crystalline free base.

Crystallization of the Boc-D-Arg-DMT-Lys(Boc)-Phe-NH$_2$ intermediate material did not show an improvement in terms of hygroscopicity, but it did allow for purification.

Example 3. HCl-IPA Deprotection of Boc-D-Arg-DMT-Lys(Boc)-Phe-NH$_2$

Equipment: A 1 L 3-neck round-bottomed flask equipped with a mechanical stirrer, thermometer, addition funnel and a nitrogen inlet.
Procedures:
Charge Boc-D-Arg-DMT-Lys(Boc)-Phe-NH$_2$ (35.4 g. 0.042 mol, 1.0 eq).
Charge IPA (280 mL, 8 parts) and begin agitation.
Adjust temperature to 22° C. (19-25° C.).
Charge 5-6 M HCl in IPA (77 mL, 0.42 mol, 10.0 eq) over a period of 10 minutes while maintaining temperature below 25° C.
Adjust temperature to 40-45° C.
Agitate mixture at 40-45° C. for a period of 1-2 h.
A sample of the mixture (ca. 0.5 mL) is removed for IPC#3 testing. Analytical methods and typical results are provided in the appropriate sections below.
IPC#3 is used to determine reaction completion as indicated by the disappearance of Boc-D-Arg-DMT-Lys(Boc)-Phe-NH$_2$ by UPLC. Limit: Report only, % a/a.
Typical results for IPC#3: Boc-D-Arg-DMT-Lys(Boc)-Phe-NH$_2$ wrt (Boc-D-Arg-DMT-Lys(Boc)-Phe-NH$_2$+ D-Arg-DMT-Lys-Phe-NH$_2$)=ND.
Cool suspension to 22° C. (19-25° C.) over a period of 1-2 h.
Filter suspension.
Wash solids with IPA (3×70 mL, 3×2 parts).
Dry on filter under a stream of N$_2$ at room temperature for a minimum of 17 h to give a white solid.
Unload the filter and weigh D-Arg-DMT-Lys-Phe-NH$_2$ solid.
Typical mass is 30.7 g, uncorrected for solvent.
A sample of the solid (ca. 250 mg) is removed for IPC#4 testing. Analytical methods and typical results are provided in the appropriate sections below.
IPC#4a is used to determine residual IPA by GC. Limit: Report only, ppm.
Typical result for IPC#5a: IPA=4.4% w/w.
IPC#4b is used to determine purity of C745 by HPLC. Limit: Report only, % a/a.
Typical result for IPC#5b: C745 purity=98.41% a/a.
Charge crude C789 to the reactor (30.7 g, 1.0 eq).
Charge MTBE (460 mL, 15 parts wrt crude C745) and begin agitation.
Charge EtOH (92 mL, 3 parts).
Adjust temperature to reflux (ca. 55° C.).
Agitate suspension at reflux temperature for a period of 16-18 h.
Adjust temperature to 22° C. (19-25° C.) over 1-2 h.
Agitate suspension at 22° C. (19-25° C.) for a period of 2-3 h.
Filter suspension.
Wash solids with MTBE (2×60 mL, 2×2 parts).
Dry on filter under a stream of N$_2$ at room temperature for a minimum of 12 h to give a white solid.

This initial process using 5-6M HCl in IPA resulted in the formation of isopropyl ester analog as well as several t-butylated analogs as impurities.

This solid required treatment with EtOH-MTBE to remove the IPA that was trapped in the solid (presumably a solvate as drying at 100° C. for extended periods of time did reduce the level below a certain amount.

Although effective at removing the iPrOH and at reducing the iPr ester content, it resulted in the formation of the ethyl ester.

Example 4. Improved Deprotection of Boc-D-Arg-DMT-Lys(Boc)-Phe-NH$_2$

A second procedure was developed using HCl in TFE with TIPS as a t-butyl cation scavenger. This procedure avoids the formation of alkyl esters but additionally reduced the number and amount of t-butylated analogs present.

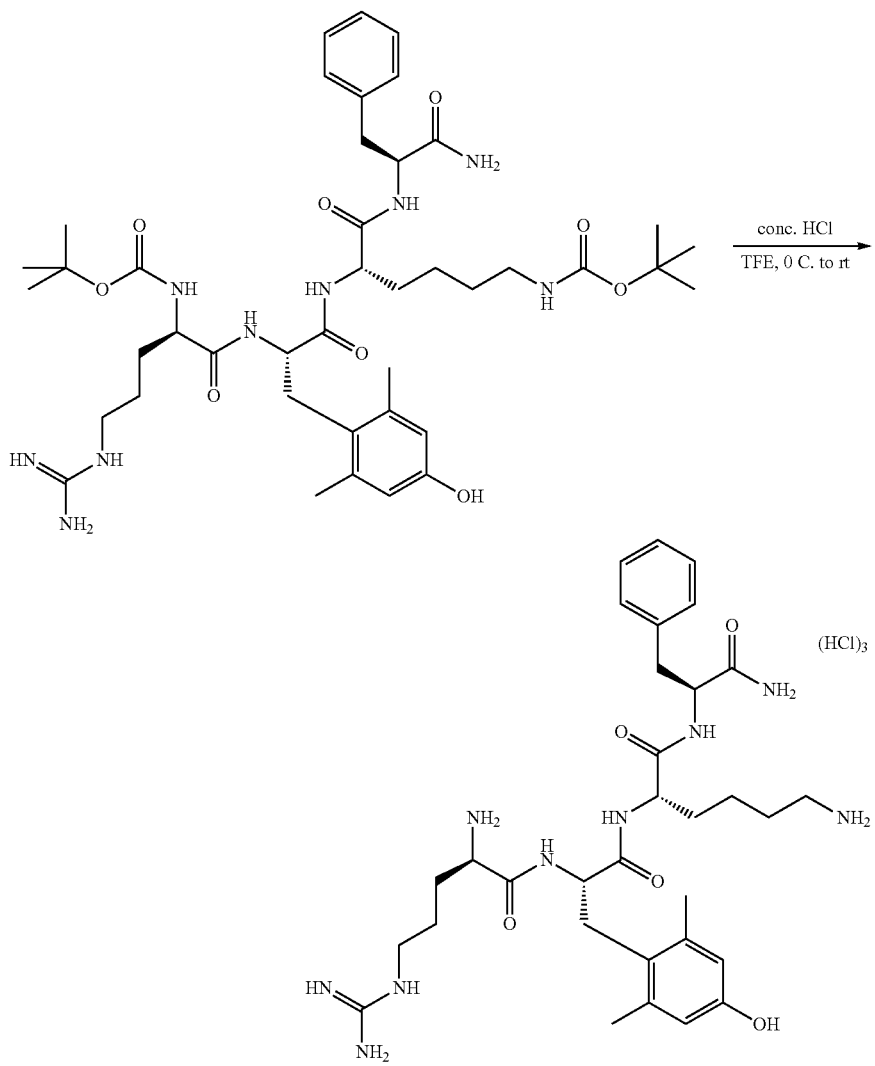

To a cooled (0-5° C.) slurry of Boc-D-Arg-DMT-Lys(Boc)-Phe-NH$_2$ (0.500 g, 0.570 mmol) and triisopropylsilane (0.584 mL, 2.85 mmol) in 2,2,2-trifluoroethanol (5.0 mL, 69 mmol) was added conc. hydrogen chloride (0.238 mL, 2.85 mmol) dropwise over approx. 5 min. After 10 min, the ice bath was removed and the mixture stirred at ambient temperature. After approx. 20 min at ambient temperature, all solids had dissolved leading to the formation of a biphasic mixture. After 1 h at ambient temperature HPLC analysis showed the consumption of Boc-D-Arg-DMT-Lys(Boc)-Phe-NH$_2$. The product purity was observed to be 98.13 area % [Agilent 1100 HPLC, Waters XSelect CSH C18, 150×4.6 mm, 3.5 micron, 1.0 ml/min, UV220 nm, Column temperature 30° C.; Solvent A: H2O (0.05% TFA); Solvent B: acetonitrile (0.05% TFA). Hold 1 min 95% A, 15 min gradient 95% to 80% A, 5 min 80% to 50% A, 5 min 50% to 10% A, hold 2 min at 10% A, 0.1 min gradient 10% to 95% A. Hold at 95% A for remainder of 36 min run time. Diluent 9:1 water/ACN]. An HPLC peak at a RRT of 1.04 was observed (0.9 area %). No TFE ester was observed by LCMS. After 90 min, the mixture was diluted with MeOAc (5 mL) affording a white precipitate. Volatiles were removed at reduced pressure and the solid concentrated from MeOAc (5 mL) to afford a free flowing white solid that was dried in vacuo overnight. Residual solvents observed by $^1$H NMR included TFE (7% w/w) and MeOAc (0.3% w/w). Product purity was 98.08 area % as assayed by HPLC. The solid was slurried in MTBE/MeOAc (2:1, 10 ml) for 10 min at 40° C., cooled to ambient temperature, filtered and dried in vacuo in a lyophilization vessel immersed in a 60° C. oil bath overnight to afford the title compound [411 mg, 96% (uncorrected for residual solvents)] as a white solid. Final product purity by HPLC was 98.07 area %. Residual solvents observed by $^1$H NMR included TFE (2.03% w/w) and MeOAc (0.19% w/w).

Example 5. XRPD Pattern of a Hydrochloride Salt of Compound I from Methano: 2-Propanol (75%: 25% v/v)

TABLE A

| Pos. [°2θ] | Height [cts] | FWHM Left [°2θ] | d-spacing [Å] | Rel. Int. [%] |
|---|---|---|---|---|
| 3.7579 | 3373.12 | 0.0768 | 23.51305 | 70.94 |
| 4.2659 | 4169.45 | 0.0895 | 20.71409 | 87.69 |
| 6.5526 | 917.62 | 0.0640 | 13.48938 | 19.30 |
| 7.2841 | 697.14 | 0.0895 | 12.13641 | 14.66 |

TABLE A-continued

| Pos. [°2θ] | Height [cts] | FWHM Left [°2θ] | d-spacing [Å] | Rel. Int. [%] |
|---|---|---|---|---|
| 8.0800 | 85.65 | 0.0900 | 10.93359 | 1.80 |
| 8.5065 | 84.96 | 0.1535 | 10.39489 | 1.79 |
| 9.7875 | 1672.39 | 0.0895 | 9.03704 | 35.17 |
| 10.6288 | 355.31 | 0.0895 | 8.32361 | 7.47 |
| 12.0543 | 189.97 | 0.1535 | 7.34226 | 4.00 |
| 12.7809 | 419.79 | 0.1279 | 6.92643 | 8.83 |
| 13.3068 | 656.50 | 0.1151 | 6.65387 | 13.81 |
| 14.1827 | 1182.25 | 0.0895 | 6.24486 | 24.86 |
| 14.5619 | 1327.04 | 0.1279 | 6.08305 | 27.91 |
| 15.0219 | 487.99 | 0.1023 | 5.89783 | 10.26 |
| 16.1288 | 613.50 | 0.2303 | 5.49546 | 12.90 |
| 16.9425 | 569.74 | 0.1535 | 5.23331 | 11.98 |
| 18.0211 | 4755.00 | 0.1151 | 4.92245 | 100.00 |
| 18.7982 | 2930.95 | 0.1407 | 4.72068 | 61.64 |
| 19.1243 | 583.81 | 0.1023 | 4.64092 | 12.28 |
| 19.6849 | 749.80 | 0.1535 | 4.51001 | 15.77 |
| 20.1376 | 596.39 | 0.1535 | 4.40963 | 12.54 |
| 20.5047 | 887.59 | 0.1535 | 4.33150 | 18.67 |
| 20.9553 | 2520.28 | 0.1151 | 4.23938 | 53.00 |
| 22.0163 | 1124.72 | 0.0895 | 4.03740 | 23.65 |
| 22.6867 | 1684.20 | 0.1279 | 3.91959 | 35.42 |
| 23.2292 | 904.36 | 0.1407 | 3.82926 | 19.02 |
| 24.0145 | 846.12 | 0.2047 | 3.70580 | 17.79 |
| 24.5746 | 412.17 | 0.1791 | 3.62258 | 8.67 |
| 25.1662 | 582.42 | 0.1279 | 3.53876 | 12.25 |
| 25.9049 | 650.36 | 0.1279 | 3.43960 | 13.68 |
| 26.4986 | 307.14 | 0.2558 | 3.36377 | 6.46 |
| 27.4092 | 275.34 | 0.1535 | 3.25405 | 5.79 |
| 27.9577 | 182.83 | 0.2047 | 3.19144 | 3.85 |
| 29.2173 | 173.31 | 0.3070 | 3.05666 | 3.64 |
| 30.4972 | 145.70 | 0.1535 | 2.93123 | 3.06 |
| 30.9418 | 102.65 | 0.0900 | 2.88773 | 2.16 |
| 31.7727 | 126.66 | 0.3070 | 2.81642 | 2.66 |
| 32.2938 | 161.36 | 0.1535 | 2.77215 | 3.39 |
| 33.4213 | 63.17 | 0.3070 | 2.68116 | 1.33 |

Example 6. XRPD Pattern of a Hydrochloride Salt of Compound I from Methanol

TABLE B

| Pos. [°2θ] | Height [cts] | FWHM Left [°2θ] | d-spacing [Å] | Rel. Int. [%] |
|---|---|---|---|---|
| 3.7036 | 1966.63 | 0.0640 | 23.85759 | 72.77 |
| 4.4432 | 2477.30 | 0.1023 | 19.88749 | 91.66 |
| 6.5634 | 704.32 | 0.0895 | 13.46726 | 26.06 |
| 7.4018 | 429.84 | 0.0512 | 11.94366 | 15.90 |
| 9.7210 | 1158.88 | 0.1023 | 9.09875 | 42.88 |
| 10.6210 | 224.51 | 0.1023 | 8.32964 | 8.31 |
| 11.0920 | 133.97 | 0.1535 | 7.97704 | 4.96 |
| 12.7331 | 103.83 | 0.0900 | 6.94660 | 3.84 |
| 13.1598 | 415.98 | 0.1023 | 6.72787 | 15.39 |
| 14.0930 | 454.88 | 0.1023 | 6.28439 | 16.83 |
| 14.7901 | 1040.30 | 0.0768 | 5.98973 | 38.49 |
| 16.7103 | 439.59 | 0.1535 | 5.30552 | 16.27 |
| 17.1509 | 141.83 | 0.0900 | 5.16593 | 5.25 |
| 18.0233 | 2702.62 | 0.1023 | 4.92186 | 100.00 |
| 18.5346 | 735.14 | 0.1023 | 4.78723 | 27.20 |
| 18.7979 | 1147.74 | 0.0640 | 4.72075 | 42.47 |
| 19.1239 | 789.29 | 0.0895 | 4.64101 | 29.20 |
| 19.5235 | 306.83 | 0.0900 | 4.54315 | 11.35 |
| 19.8085 | 422.15 | 0.1023 | 4.48213 | 15.62 |
| 20.1544 | 324.59 | 0.1535 | 4.40598 | 12.01 |
| 20.6070 | 478.45 | 0.1023 | 4.31022 | 17.70 |
| 20.8573 | 1011.67 | 0.0640 | 4.25907 | 37.43 |
| 21.3109 | 537.54 | 0.1535 | 4.16942 | 19.89 |
| 22.0189 | 619.33 | 0.2303 | 4.03694 | 22.92 |
| 22.6758 | 1060.70 | 0.1023 | 3.92146 | 39.25 |
| 23.0757 | 398.04 | 0.1535 | 3.85439 | 14.73 |
| 23.6744 | 38.83 | 0.0900 | 3.75515 | 1.44 |
| 23.9728 | 340.14 | 0.1791 | 3.71215 | 12.59 |
| 24.4777 | 293.52 | 0.1535 | 3.63671 | 10.86 |

TABLE B-continued

| Pos. [°2θ] | Height [cts] | FWHM Left [°2θ] | d-spacing [Å] | Rel. Int. [%] |
|---|---|---|---|---|
| 25.7316 | 132.83 | 0.0900 | 3.45941 | 4.91 |
| 26.4407 | 215.92 | 0.2047 | 3.37100 | 7.99 |
| 27.7972 | 173.31 | 0.1791 | 3.20950 | 6.41 |
| 30.1162 | 99.20 | 0.2047 | 2.96744 | 3.67 |
| 32.1646 | 67.76 | 0.3070 | 2.78299 | 2.51 |

Example 7. XRPD Pattern of a Tosylate Salt of Compound I from Acetone

TABLE C

| Pos. [°2Th.] | Height [cts] | FWHM [°2Th.] | d-spacing [Å] | Rel. Int. [%] |
|---|---|---|---|---|
| 5.1621 | 2149.15 | 0.1663 | 17.11956 | 100.00 |
| 8.9359 | 438.04 | 0.2303 | 9.89635 | 20.38 |
| 10.7664 | 184.28 | 0.2047 | 8.21754 | 8.57 |
| 13.3445 | 266.11 | 0.2047 | 6.63517 | 12.38 |
| 14.3884 | 539.35 | 0.4605 | 6.15602 | 25.10 |
| 15.9863 | 161.64 | 0.2558 | 5.54412 | 7.52 |
| 17.2952 | 407.57 | 0.2558 | 5.12739 | 18.96 |
| 18.8443 | 420.10 | 0.2047 | 4.70925 | 19.55 |
| 19.5521 | 362.22 | 0.1535 | 4.54033 | 16.85 |
| 21.0051 | 693.10 | 0.1535 | 4.22943 | 32.25 |
| 23.2998 | 206.42 | 0.3582 | 3.81783 | 9.60 |
| 24.6506 | 86.12 | 0.5117 | 3.61159 | 4.01 |

Example 8. XRPD Pattern of a Mesylate Salt of Compound I from Acetone

TABLE D

| Pos. [°2Th.] | Height [cts] | FWHM [°2Th.] | d-spacing [Å] | Rel. Int. [%] |
|---|---|---|---|---|
| 5.4291 | 3079.02 | 0.0384 | 16.27808 | 100.00 |
| 8.0335 | 120.51 | 0.1535 | 11.00580 | 3.91 |
| 9.0773 | 115.67 | 0.2558 | 9.74250 | 3.76 |
| 10.8149 | 293.11 | 0.1279 | 8.18074 | 9.52 |
| 13.4288 | 415.08 | 0.1279 | 6.59369 | 13.48 |
| 14.7938 | 421.32 | 0.2558 | 5.98822 | 13.68 |
| 15.7960 | 318.03 | 0.1791 | 5.61049 | 10.33 |
| 17.5693 | 431.98 | 0.1535 | 5.04800 | 14.03 |
| 18.9795 | 376.14 | 0.1279 | 4.67599 | 12.22 |
| 19.6937 | 289.54 | 0.2047 | 4.50799 | 9.40 |
| 21.3056 | 720.36 | 0.2303 | 4.17044 | 23.40 |
| 22.2563 | 263.14 | 0.1535 | 3.99442 | 8.55 |
| 24.1299 | 237.45 | 0.7164 | 3.68833 | 7.71 |
| 25.7352 | 135.39 | 0.3070 | 3.46180 | 4.40 |
| 27.6495 | 84.81 | 0.4093 | 3.22631 | 2.75 |
| 30.9496 | 17.50 | 0.6140 | 2.88941 | 0.57 |

Example 9. XRPD Pattern of an Oxalate Salt of Compound I from Acetone

TABLE E

| Pos. [°2θ] | Height [cts] | FWHM Left [°2θ] | d-spacing [Å] | Rel. Int. [%] |
|---|---|---|---|---|
| 4.0824 | 291.09 | 0.1023 | 21.64476 | 10.42 |
| 7.2188 | 323.51 | 0.1279 | 12.24600 | 11.58 |
| 7.7660 | 749.77 | 0.1023 | 11.38428 | 26.85 |
| 8.1685 | 455.55 | 0.0768 | 10.82427 | 16.31 |
| 8.7856 | 126.66 | 0.1023 | 10.06525 | 4.54 |

TABLE E-continued

| Pos. [°2θ] | Height [cts] | FWHM Left [°2θ] | d-spacing [Å] | Rel. Int. [%] |
|---|---|---|---|---|
| 10.1057 | 979.70 | 0.0768 | 8.75327 | 35.08 |
| 11.7275 | 233.13 | 0.1023 | 7.54614 | 8.35 |
| 12.0519 | 307.19 | 0.1023 | 7.34374 | 11.00 |
| 12.2864 | 248.60 | 0.1023 | 7.20411 | 8.90 |
| 12.7774 | 846.47 | 0.1023 | 6.92837 | 30.31 |
| 13.2740 | 468.08 | 0.0768 | 6.67023 | 16.76 |
| 13.6796 | 175.54 | 0.1535 | 6.47336 | 6.29 |
| 14.4861 | 387.62 | 0.1151 | 6.11472 | 13.88 |
| 14.9214 | 326.40 | 0.1151 | 5.93732 | 11.69 |
| 15.1377 | 150.25 | 0.0900 | 5.84810 | 5.38 |
| 15.5347 | 106.18 | 0.0900 | 5.69954 | 3.80 |
| 16.1829 | 161.09 | 0.1535 | 5.47721 | 5.77 |
| 17.7646 | 1786.25 | 0.1151 | 4.99295 | 63.96 |
| 18.1548 | 399.21 | 0.1407 | 4.88652 | 14.30 |
| 18.5392 | 2792.57 | 0.0895 | 4.78604 | 100.00 |
| 18.9751 | 574.37 | 0.1023 | 4.67707 | 20.57 |
| 19.9095 | 1049.25 | 0.1023 | 4.45962 | 37.57 |
| 20.3639 | 672.05 | 0.1535 | 4.36113 | 24.07 |
| 21.0328 | 208.25 | 0.2047 | 4.22393 | 7.46 |
| 21.9414 | 400.27 | 0.0900 | 4.04767 | 14.33 |
| 21.9676 | 539.10 | 0.1023 | 4.04624 | 19.30 |
| 22.2732 | 718.09 | 0.1535 | 3.99141 | 25.71 |
| 22.8116 | 257.00 | 0.1535 | 3.89841 | 9.20 |
| 23.3197 | −104.04 | 0.0900 | 3.81146 | −3.73 |
| 23.5325 | 291.26 | 0.1279 | 3.78060 | 10.43 |
| 24.0190 | 147.43 | 0.1535 | 3.70511 | 5.28 |
| 24.8019 | 132.93 | 0.3070 | 3.58990 | 4.76 |
| 25.2913 | 145.65 | 0.2303 | 3.52153 | 5.22 |
| 25.6339 | 162.92 | 0.2047 | 3.47524 | 5.83 |
| 26.6566 | 202.58 | 0.2047 | 3.34419 | 7.25 |
| 27.7426 | 83.70 | 0.1535 | 3.21570 | 3.00 |
| 28.2705 | 228.59 | 0.1279 | 3.15684 | 8.19 |
| 28.9314 | 78.20 | 0.0900 | 3.08365 | 2.80 |
| 29.2563 | 124.89 | 0.2047 | 3.05267 | 4.47 |
| 30.0846 | 91.09 | 0.1535 | 2.97049 | 3.26 |
| 30.7947 | 123.92 | 0.2047 | 2.90359 | 4.44 |
| 31.5899 | 127.84 | 0.1535 | 2.83229 | 4.58 |
| 31.9371 | 93.79 | 0.0900 | 2.79997 | 3.36 |
| 32.8553 | 71.65 | 0.2047 | 2.72605 | 2.57 |

Example 10. XRPD Pattern of a Benzoate Salt of Compound I f from Methanol

TABLE F

| Pos. [°2θ] | Height [cts] | FWHM Left [°2θ] | d-spacing [Å] | Rel. Int. [%] |
|---|---|---|---|---|
| 3.6742 | 2073.90 | 0.0768 | 24.04811 | 100.00 |
| 4.4204 | 1347.38 | 0.0895 | 19.99017 | 64.97 |
| 6.7177 | 829.29 | 0.0768 | 13.15834 | 39.99 |
| 7.0320 | 229.18 | 0.0768 | 12.57092 | 11.05 |
| 8.2133 | 416.05 | 0.0895 | 10.76529 | 20.06 |
| 9.8583 | 662.53 | 0.0895 | 8.97235 | 31.95 |
| 10.2604 | 109.77 | 0.0900 | 8.61446 | 5.29 |
| 12.3942 | 500.02 | 0.1023 | 7.14170 | 24.11 |
| 13.2923 | 979.35 | 0.0895 | 6.66111 | 47.22 |
| 13.6972 | 1012.99 | 0.1023 | 6.46510 | 48.84 |
| 14.1013 | 1154.57 | 0.1023 | 6.28071 | 55.67 |
| 14.6960 | 340.34 | 0.2047 | 6.02788 | 16.41 |
| 15.7923 | 726.93 | 0.1023 | 5.61180 | 35.05 |
| 16.4926 | 394.77 | 0.1023 | 5.37505 | 19.04 |
| 17.0775 | 509.25 | 0.0768 | 5.19226 | 24.56 |
| 17.2537 | 552.89 | 0.1279 | 5.13961 | 26.66 |
| 18.0813 | 1729.49 | 0.1279 | 4.90621 | 83.39 |
| 18.4075 | 885.37 | 0.1279 | 4.81999 | 42.69 |
| 18.9537 | 1288.35 | 0.1279 | 4.68231 | 62.12 |
| 19.5451 | 747.42 | 0.1279 | 4.54194 | 36.04 |
| 19.7885 | 486.20 | 0.1023 | 4.48661 | 23.44 |
| 20.2166 | 505.95 | 0.1279 | 4.39256 | 24.40 |
| 20.6718 | 1051.62 | 0.1407 | 4.29685 | 50.71 |
| 20.8819 | 961.73 | 0.1279 | 4.25411 | 46.37 |
| 21.6381 | 545.53 | 0.1023 | 4.10712 | 26.30 |

TABLE F-continued

| Pos. [°2θ] | Height [cts] | FWHM Left [°2θ] | d-spacing [Å] | Rel. Int. [%] |
|---|---|---|---|---|
| 22.2851 | 1623.89 | 0.1535 | 3.98930 | 78.30 |
| 22.6611 | 298.77 | 0.0900 | 3.92072 | 14.41 |
| 23.0749 | 506.06 | 0.1535 | 3.85453 | 24.40 |
| 24.3020 | 1218.36 | 0.1407 | 3.66260 | 58.75 |
| 24.7773 | 408.23 | 0.2047 | 3.59341 | 19.68 |
| 25.5656 | 337.24 | 0.2558 | 3.48437 | 16.26 |
| 26.6658 | 206.54 | 0.1535 | 3.34305 | 9.96 |
| 27.2542 | 199.90 | 0.2558 | 3.27220 | 9.64 |
| 27.7067 | 201.69 | 0.1535 | 3.21978 | 9.72 |
| 28.3209 | 285.54 | 0.2558 | 3.15134 | 13.77 |
| 29.3217 | 120.66 | 0.2047 | 3.04602 | 5.82 |
| 30.1348 | 153.42 | 0.4093 | 2.96566 | 7.40 |
| 30.4172 | 195.25 | 0.1535 | 2.93876 | 9.41 |
| 31.1772 | 176.27 | 0.3070 | 2.86884 | 8.50 |
| 32.4960 | 59.94 | 0.7164 | 2.75536 | 2.89 |
| 33.6018 | 144.00 | 0.1791 | 2.66717 | 6.94 |

INCORPORATION BY REFERENCE

All of the U.S. patents and U.S. and PCT published patent applications cited herein are hereby incorporated by reference.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:
1. A crystalline form of a salt of Compound I,

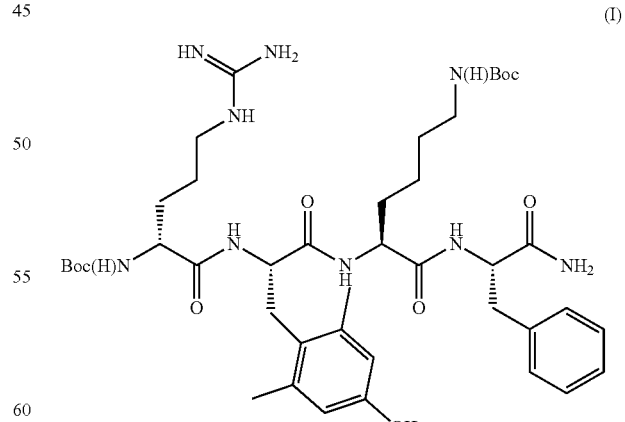

(Boc-D-Arg-DMT-Lys(Boc)-Phe-NH$_2$; (I)),
wherein said crystalline form has characteristic peaks in its XRPD pattern at values of two theta as described in any one of Tables A'-F' or shown in any one of FIGS. 9-14;

wherein Table A' is:

| Pos. [°2θ] |
| --- |
| 3.7579 |
| 4.2659 |
| 6.5526 |
| 7.2841 |
| 8.0800 |
| 8.5065 |
| 9.7875 |
| 10.6288 |
| 12.0543 |
| 12.7809 |
| 13.3068 |
| 14.1827 |
| 14.5619 |
| 15.0219 |
| 16.1288 |
| 16.9425 |
| 18.0211 |
| 18.7982 |
| 19.1243 |
| 19.6849 |
| 20.1376 |
| 20.5047 |
| 20.9553 |
| 22.0163 |
| 22.6867 |
| 23.2292 |
| 24.0145 |
| 24.5746 |
| 25.1662 |
| 25.9049 |
| 26.4986 |
| 27.4092 |
| 27.9577 |
| 29.2173 |
| 30.4972 |
| 30.9418 |
| 31.7727 |
| 32.2938 |
| 33.4213; |

Table B' is:

| Pos. [°2θ] |
| --- |
| 3.7036 |
| 4.4432 |
| 6.5634 |
| 7.4018 |
| 9.7210 |
| 10.6210 |
| 11.0920 |
| 12.7331 |
| 13.1598 |
| 14.0930 |
| 14.7901 |
| 16.7103 |
| 17.1509 |
| 18.0233 |
| 18.5346 |
| 18.7979 |
| 19.1239 |
| 19.5235 |
| 19.8085 |
| 20.1544 |
| 20.6070 |
| 20.8573 |
| 21.3109 |
| 22.0189 |
| 22.6758 |
| 23.0757 |
| 23.6744 |
| 23.9728 |
| 24.4777 |
| 25.7316 |

| Pos. [°2θ] |
| --- |
| 26.4407 |
| 27.7972 |
| 30.1162 |
| 32.1646; |

Table C' is:

| Pos. [°2θ] |
| --- |
| 5.1621 |
| 8.9359 |
| 10.7664 |
| 13.3445 |
| 14.3884 |
| 15.9863 |
| 17.2952 |
| 18.8443 |
| 19.5521 |
| 21.0051 |
| 23.2998 |
| 24.6506; |

Table D' is:

| Pos. [°2θ] |
| --- |
| 5.4291 |
| 8.0335 |
| 9.0773 |
| 10.8149 |
| 13.4288 |
| 14.7938 |
| 15.7960 |
| 17.5693 |
| 18.9795 |
| 19.6937 |
| 21.3056 |
| 22.2563 |
| 24.1299 |
| 25.7352 |
| 27.6495 |
| 30.9496; |

Table E' is:

| Pos. [°2θ] |
| --- |
| 4.0824 |
| 7.2188 |
| 7.7660 |
| 8.1685 |
| 8.7856 |
| 10.1057 |
| 11.7275 |
| 12.0519 |
| 12.2864 |
| 12.7774 |
| 13.2740 |
| 13.6796 |
| 14.4861 |
| 14.9214 |
| 15.1377 |
| 15.5347 |
| 16.1829 |
| 17.7646 |
| 18.1548 |
| 18.5392 |
| 18.9751 |
| 19.9095 |
| 20.3639 |

55
-continued

| Pos. [°2θ] |
|---|
| 21.0328 |
| 21.9414 |
| 21.9676 |
| 22.2732 |
| 22.8116 |
| 23.3197 |
| 23.5325 |
| 24.0190 |
| 24.8019 |
| 25.2913 |
| 25.6339 |
| 26.6566 |
| 27.7426 |
| 28.2705 |
| 28.9314 |
| 29.2563 |
| 30.0846 |
| 30.7947 |
| 31.5899 |
| 31.9371 |
| 32.8553; |

Table F' is:

| Pos. [°2θ] |
|---|
| 3.6742 |
| 4.4204 |
| 6.7177 |
| 7.0320 |
| 8.2133 |
| 9.8583 |
| 10.2604 |
| 12.3942 |
| 13.2923 |
| 13.6972 |
| 14.1013 |
| 14.6960 |
| 15.7923 |
| 16.4926 |
| 17.0775 |
| 17.2537 |
| 18.0813 |
| 18.4075 |
| 18.9537 |
| 19.5451 |
| 19.7885 |
| 20.2166 |
| 20.6718 |
| 20.8819 |
| 21.6381 |
| 22.2851 |
| 22.6611 |
| 23.0749 |
| 24.3020 |
| 24.7773 |
| 25.5656 |
| 26.6658 |
| 27.2542 |
| 27.7067 |
| 28.3209 |
| 29.3217 |
| 30.1348 |
| 30.4172 |

56
-continued

| Pos. [°2θ] |
|---|
| 31.1772 |
| 32.4960 |
| 33.6018. |

2. A crystalline form of a hydrochloride salt of Compound I,

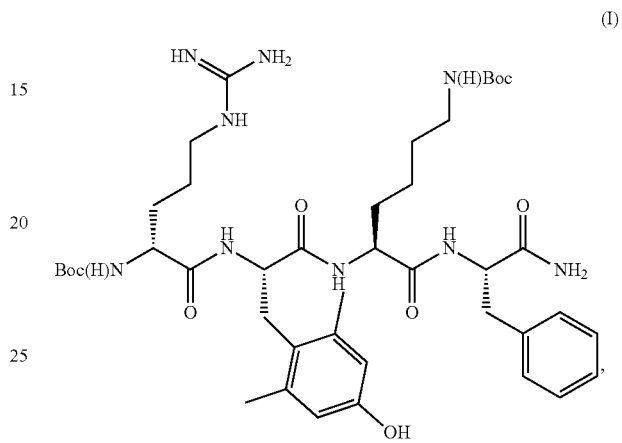

(I)

wherein said crystalline form has characteristic peaks in its XRPD pattern at values of two theta (° 2θ) of: 3.8, 4.3, 9.8, 14.6, 18.0, 18.8, 20.9, and 22.7.

3. The crystalline form of claim 2, wherein said crystalline form has characteristic peaks in its XRPD pattern at values of two theta (° 2θ) of: 3.8, 4.3, 6.5, 7.3, 9.8, 13.3, 14.2, 14.6, 16.1, 16.9, 18.0, 18.8, 19.1, 19.7, 20.1, 20.5, 20.9, 22.0, 22.7, 23.2, 24.0, 25.2, and 25.9.

4. A crystalline form of a hydrochloride salt of Compound I,

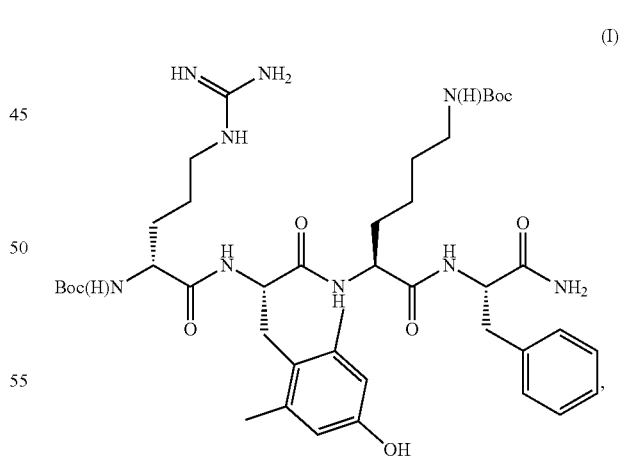

(I)

wherein said crystalline form has characteristic peaks in its XRPD pattern at values of two theta (° 2θ) of: 3.7, 4.4, 6.6, 9.7, 14.8, 18.0, 18.5, 18.8, 19.1, 20.9, and 22.7.

5. The crystalline form of claim 4, wherein said crystalline form has characteristic peaks in its XRPD pattern at values of two theta (° 2θ) of: 3.7, 4.4, 6.6, 7.4, 9.7, 10.6, 13.2, 14.1, 14.8, 16.7, 18.0, 18.5, 18.8, 19.1, 19.5, 19.8, 20.1, 20.6, 20.9, 21.3, 22.0, 22.7, 23.1, and 24.0.

6. A crystalline form of a tosylate salt of Compound I,

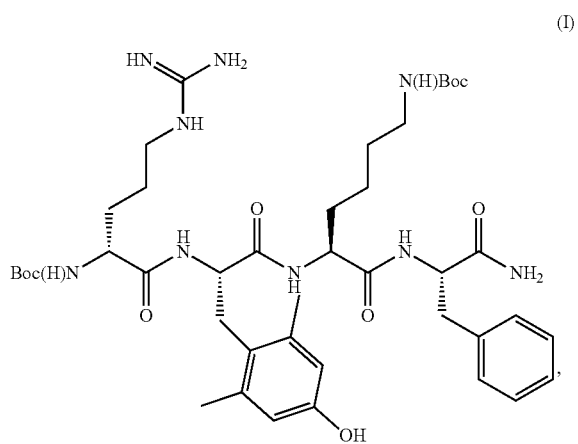

(I)

wherein said crystalline form has characteristic peaks in its XRPD pattern at values of two theta (° 2θ) of: 5.2, 8.9, 14.4, 17.3, 18.8, 19.5, and 21.0.

7. The crystalline form of claim 6, wherein said crystalline form has characteristic peaks in its XRPD pattern at values of two theta (° 2θ) of: 5.2, 8.9, 10.8, 13.4, 14.4, 16.0, 17.3, 18.8, 19.5, 21.0, 23.3, and 24.6.

8. A crystalline form of a mesylate salt of Compound I,

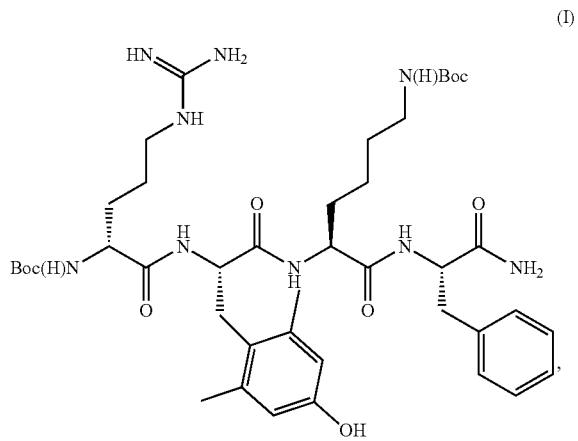

(I)

wherein said crystalline form has characteristic peaks in its XRPD pattern at values of two theta (° 2θ) of: 5.4, 13.4, 14.8, 15.8, 17.6, 19.0, and 21.3.

9. The crystalline form of claim 8, wherein said crystalline form has characteristic peaks in its XRPD pattern at values of two theta (° 2θ) of: 5.4, 10.8, 13.4, 14.8, 15.8, 17.6, 19.0, 19.7, 21.3, 22.3, 24.1, and 25.7.

10. A crystalline form of an oxalate salt of Compound I,

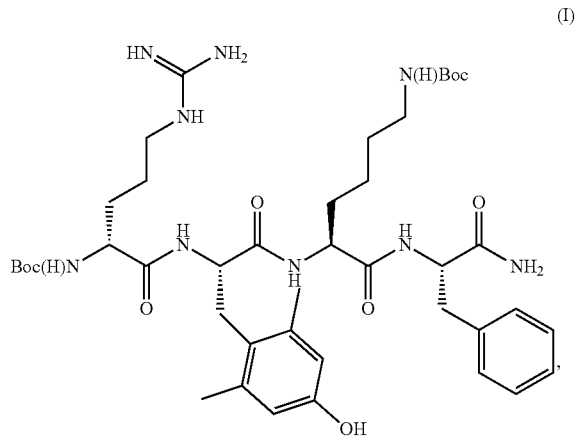

(I)

wherein said crystalline form has characteristic peaks in its XRPD pattern at values of two theta (° 2θ) of: 7.8, 10.1, 12.8, 17.8, 18.5, 19.9, and 22.3.

11. The crystalline form of an oxalate salt of claim 10, wherein said crystalline form has characteristic peaks in its XRPD pattern at values of two theta (° 2θ) of: 4.1, 7.2, 7.8, 8.1, 10.1, 12.0, 12.8, 13.3, 14.5, 14.9, 17.8, 18.1. 18.5, 19.9, 20.4, 21.9, 22.0, 22.3, and 23.5.

12. A crystalline form of a benzoate salt of Compound I,

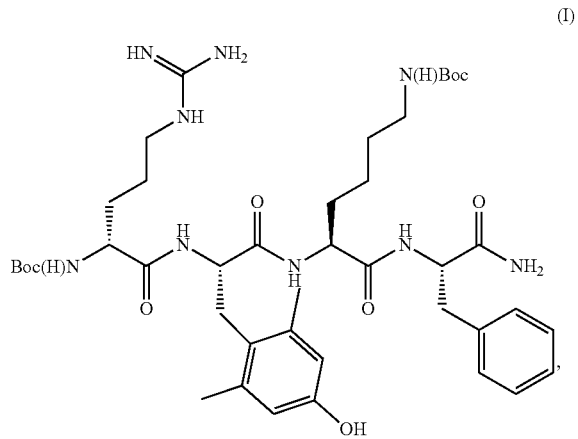

(I)

wherein said crystalline form has characteristic peaks in its XRPD pattern at values of two theta (° 2θ) of: 3.7, 4.4, 14.1, 18.1, 18.9, 20.7, 22.3, and 24.3.

13. The crystalline form of claim 12, wherein said crystalline form has characteristic peaks in its XRPD pattern at values of two theta (° 2θ) of: 3.7, 4.4, 6.7, 9.9, 13.3, 13.7, 14.1, 15.8, 17.2, 18.1, 18.4, 18.9, 19.5, 20.7, 20.9, 21.6, 22.3, and 24.3.

14. The crystalline form of claim 1, wherein said crystalline form has characteristic peaks its XRPD pattern at values of two theta as described in any one of Tables A' and C'-F'.

* * * * *